(12) United States Patent
Cetti et al.

(10) Patent No.: US 11,938,349 B2
(45) Date of Patent: Mar. 26, 2024

(54) ANTIPERSPIRANT AND DEODORANT COMPOSITIONS COMPRISING CAPSULES

(71) Applicant: The Procter & Gamble Company, Cincinnati, OH (US)

(72) Inventors: Jonathan Robert Cetti, Mason, OH (US); Andre Martim Barros, Woluwe Saint Etienne (BE); Mariana B T Cardoso, Brussels (BE); Johan Smets, Lubbeek (BE); Steven Daryl Smith, Fairfield, OH (US); Pierre Daniel Verstraete, Woluwe Saint Lambert (BE); Valerie Wong, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 150 days.

(21) Appl. No.: 17/500,984

(22) Filed: Oct. 14, 2021

(65) Prior Publication Data

US 2022/0118287 A1    Apr. 21, 2022

Related U.S. Application Data

(60) Provisional application No. 63/092,592, filed on Oct. 16, 2020.

(51) Int. Cl.
*A61Q 15/00* (2006.01)
*A61K 8/02* (2006.01)
(Continued)

(52) U.S. Cl.
CPC ............ *A61Q 15/00* (2013.01); *A61K 8/0233* (2013.01); *A61K 8/06* (2013.01); *A61K 8/25* (2013.01); *A61K 8/26* (2013.01); *A61K 8/34* (2013.01); *A61K 8/585* (2013.01); *A61K 2800/34* (2013.01); *A61K 2800/412* (2013.01); *A61K 2800/413* (2013.01); *A61K 2800/56* (2013.01); *A61K 2800/805* (2013.01)

(58) Field of Classification Search
CPC ........ A61Q 15/00; A61K 8/0233; A61K 8/06; A61K 8/25; A61K 8/26; A61K 8/34; A61K 8/585; A61K 2800/34; A61K 2800/412; A61K 2800/413; A61K 2800/56; A61K 2800/805
See application file for complete search history.

(56) References Cited

U.S. PATENT DOCUMENTS

| 5,500,223 A | 3/1996 | Behan et al. |
| 6,243,909 B1 | 6/2001 | Graham et al. |

(Continued)

FOREIGN PATENT DOCUMENTS

| CA | 2980792 A1 | 2/2010 |
| CN | 103432970 A | 12/2013 |

(Continued)

OTHER PUBLICATIONS

15902 PCT Search Report and Written Opinion for PCT/US2021/071852 dated Mar. 7, 2022, 14 pages.

(Continued)

*Primary Examiner* — Ling Siu Choi
*Assistant Examiner* — Ronald Grinsted
(74) *Attorney, Agent, or Firm* — Alexandra S. Anoff

(57) ABSTRACT

Antiperspirant and deodorant compositions that include capsules characterized by substantially inorganic shells. The present disclosure further relates to methods of making and using such compositions.

20 Claims, 3 Drawing Sheets

(51) Int. Cl.
*A61K 8/06* (2006.01)
*A61K 8/25* (2006.01)
*A61K 8/26* (2006.01)
*A61K 8/34* (2006.01)
*A61K 8/58* (2006.01)

(56) References Cited

U.S. PATENT DOCUMENTS

| | | |
|---|---|---|
| 6,537,583 B1 | 3/2003 | Dupuis et al. |
| 8,425,940 B2 | 4/2013 | Lapidot et al. |
| 8,931,971 B2 | 1/2015 | Schwarz et al. |
| 9,603,784 B2 | 3/2017 | Shimizu et al. |
| 10,046,291 B2 | 8/2018 | Yamazaki |
| 10,285,928 B2 | 5/2019 | Marsh et al. |
| 2004/0163674 A1 | 8/2004 | Policicchio et al. |
| 2005/0158369 A1 | 7/2005 | Dorschner et al. |
| 2006/0188551 A1 | 8/2006 | Hauser et al. |
| 2008/0096780 A1 | 4/2008 | Veugelers et al. |
| 2009/0247449 A1 | 10/2009 | Burdis |
| 2010/0143422 A1 | 6/2010 | Popplewell et al. |
| 2010/0247660 A1 | 9/2010 | Lei et al. |
| 2011/0104221 A1 | 5/2011 | Galeone et al. |
| 2011/0118161 A1 | 5/2011 | Looft |
| 2011/0177951 A1 | 7/2011 | Toledano |
| 2012/0104639 A1 | 5/2012 | Traynor et al. |
| 2012/0128747 A1 | 5/2012 | Veronique et al. |
| 2012/0202695 A1 | 8/2012 | Toledano |
| 2012/0237578 A1 | 9/2012 | Lei |
| 2013/0040871 A1 | 2/2013 | Dreher |
| 2014/0044761 A1 | 2/2014 | Lei et al. |
| 2014/0331414 A1 | 11/2014 | Bone |
| 2014/0338134 A1 | 11/2014 | Fernandez Prieto et al. |
| 2014/0342972 A1 | 11/2014 | Smets |
| 2016/0168509 A1 | 6/2016 | Hitchcock |
| 2016/0168510 A1 | 6/2016 | Tasker et al. |
| 2016/0168511 A1 | 6/2016 | Hitchcock et al. |
| 2016/0184196 A1 | 6/2016 | Baxter et al. |
| 2016/0303531 A1 | 10/2016 | Yamazaki |
| 2016/0317993 A1 | 11/2016 | Rotello et al. |
| 2018/0085291 A1 | 3/2018 | Sasaki |
| 2018/0207451 A1 | 7/2018 | Toledano |
| 2018/0339176 A1 | 11/2018 | Toledano |
| 2020/0114328 A1 | 4/2020 | Jerri et al. |
| 2020/0129947 A1 | 4/2020 | Ouali et al. |
| 2020/0255776 A1 | 8/2020 | Schmiedel et al. |
| 2020/0330948 A1 | 10/2020 | Cardoso et al. |
| 2020/0330949 A1 | 10/2020 | Cardoso et al. |
| 2020/0330950 A1 | 10/2020 | Cardoso et al. |
| 2022/0118417 A1 | 4/2022 | Smith et al. |
| 2022/0119741 A1 | 4/2022 | Smets et al. |
| 2022/0119742 A1 | 4/2022 | Smets et al. |
| 2022/0119743 A1 | 4/2022 | Barros et al. |
| 2022/0258118 A1 | 8/2022 | Cardoso et al. |

FOREIGN PATENT DOCUMENTS

| | | |
|---|---|---|
| CN | 105612248 A | 5/2016 |
| CN | 105734540 A | 7/2016 |
| CN | 107001979 A | 6/2017 |
| CN | 107249545 B | 5/2021 |
| EP | 1767613 A1 | 3/2007 |
| EP | 1767614 A1 | 3/2007 |
| EP | 2078696 A1 | 7/2009 |
| EP | 3181674 A1 | 6/2017 |
| EP | 2865423 B1 | 3/2020 |
| WO | 0145615 A1 | 6/2001 |
| WO | 2005044220 A1 | 5/2005 |
| WO | 2007019201 A1 | 2/2007 |
| WO | 2009106318 A2 | 9/2009 |
| WO | 2011154421 A1 | 12/2011 |
| WO | 2013078551 A1 | 6/2013 |
| WO | 2013083760 A2 | 6/2013 |
| WO | 2013174921 A1 | 11/2013 |
| WO | 2016100477 A1 | 6/2016 |
| WO | 2016100479 A1 | 6/2016 |
| WO | 2017016636 A1 | 2/2017 |
| WO | 2017075074 A1 | 5/2017 |
| WO | 2018189588 A1 | 10/2018 |
| WO | 2018231886 A1 | 12/2018 |
| WO | 2020077451 A1 | 4/2020 |
| WO | 2020214876 A1 | 10/2020 |
| WO | 2020214877 A1 | 10/2020 |
| WO | 2020214878 A1 | 10/2020 |

OTHER PUBLICATIONS

15507 PCT Search Report and Written Opinion for PCT/US2020/028619; dated Jun. 30, 2020, 18 pages.
15508 PCT Search Report and Written Opinion for PCT/US2020/028621; dated Jul. 7, 2020, 13 pages.
15509 PCT Search Report and Written Opinion for PCT/US2020/028623 ; dated Jul. 21, 2020, 14 pages.
All Office Actions; U.S. Appl. No. 16/851,176, filed Apr. 17, 2020.
All Office Actions; U.S. Appl. No. 16/851,194, filed Apr. 17, 2020.
All Office Actions; U.S. Appl. No. 16/851,173, filed Apr. 17, 2020.
All Office Actions; U.S. Appl. No. 17/500,970, filed Oct. 14, 2021.
All Office Actions; U.S. Appl. No. 17/500,979, filed Oct. 14, 2021.
All Office Actions; U.S. Appl. No. 17/501,186, filed Oct. 14, 2021.
Jyothi et al., "Microencapsulation techniques, factors influencing encapsulation efficiency", Journal of Microencapsulation, 27:3, pp. 187-197.
Liu, M.: "Understanding the mechanicalstrength of micro capsules and their adhesion on fabric surfaces",2010, University of Birmingham, XP055511234, cited in the application pp. 86-89 p. 104-p. 106 p. 118.
Thompson et al., "Colloidosomes: Synthesis, properties and applications", Journal of Colloid and Interface Science, 447, 2015, pp. 217-228.
Unpublished U.S. Appl. No. 17/500,970, filed Oct. 14, 2021, to Andre Martim Barros et al.
Unpublished U.S. Appl. No. 17/500,979, filed Oct. 14, 2021, to Andre Martim Barros et al.
Unpublished U.S. Appl. No. 17/501,186, filed Oct. 14, 2021, to Srinivas Krishnaswamy Mirle.
All Office Actions; U.S. Appl. No. 17/498,016, filed Oct. 11, 2021.
All Office Actions; U.S. Appl. No. 17/501,202, filed Oct. 14, 2021.
All Office Actions; U.S. Appl. No. 17/727,857, filed Apr. 25, 2022.
All Office Actions; U.S. Appl. No. 18/115,890, filed Mar. 1, 2023.
Unpublished U.S. Appl. No. 18/115,890, filed Mar. 1, 2023, to Mariana B T Cardoso et. al.

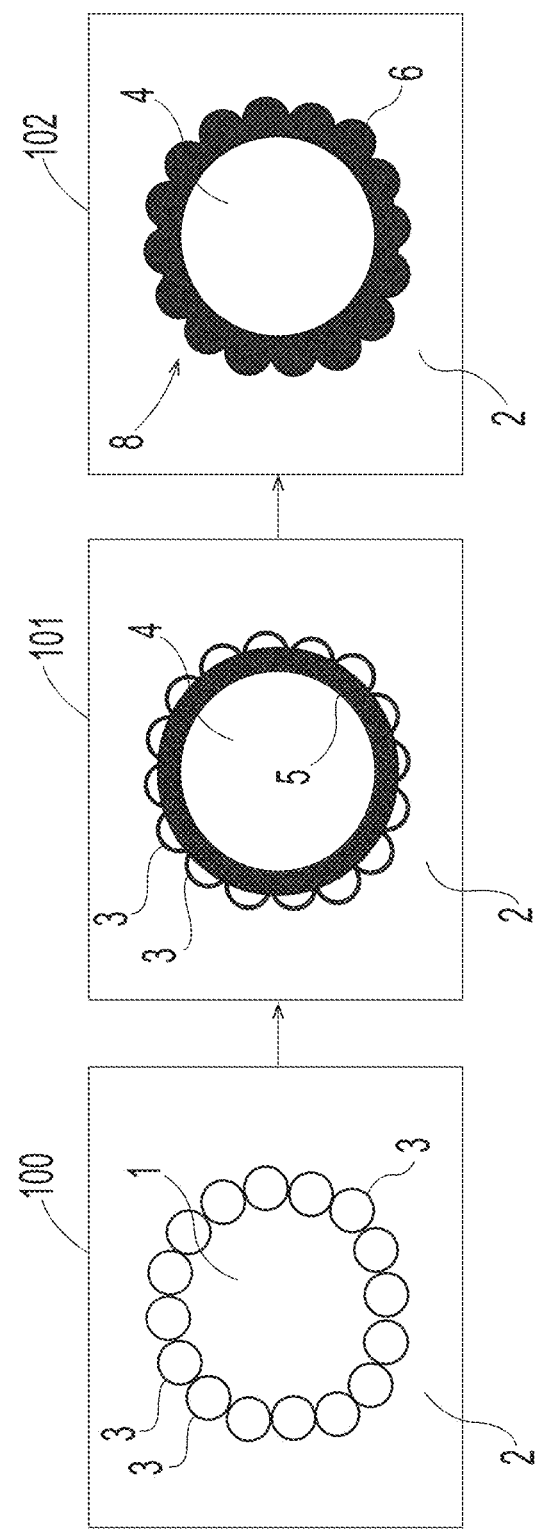

ANTIPERSPIRANT AND DEODORANT COMPOSITIONS COMPRISING CAPSULES

FIELD OF THE INVENTION

The present disclosure relates to antiperspirants and deodorants that include certain capsules characterized by substantially inorganic shells. The present disclosure further relates to methods of making and using such compositions.

BACKGROUND OF THE INVENTION

Many antiperspirant and deodorant products are formulated with perfumed core/shell capsules. Typically, the cores of such capsules include perfume, and the shell often comprises a polymeric material such as an aminoplast, a polyurea, or a polyacrylate. These capsules are useful in delivering the benefit agent to a target surface, such as the skin. While on the skin, the capsules will rupture, releasing the perfume. However, sometimes the perfume capsules can leak before the ideal time to be released, thereby reducing the efficiency of the perfume delivery system.

Furthermore, the perfumes typically include a variety of perfume raw materials ("PRMs"). Problematically, different PRMs may leak at different rates through the capsule wall. Over time, such as while the product is being transported or stored, the character of the perfume can change due to some PRMs leaking more than others. This can lead to olfactory experiences that are less desirable than what the manufacturer formulated for, quality control issues, and even consumer dissatisfaction when the freshness profile provided by the first dose of the product is different than that provided by the last dose.

There is a need for antiperspirant and deodorant products that include perfume delivery systems that have improved perfume leakage profiles.

SUMMARY OF THE INVENTION

An antiperspirant or deodorant composition comprising
a population of capsules,
the capsules comprising a core and a shell surrounding the core,
wherein the core comprises perfume raw materials,
wherein the shell comprises:
a substantially inorganic first shell component comprising
a condensed layer and a nanoparticle layer, wherein the condensed layer comprises a condensation product of a precursor,
wherein the nanoparticle layer comprises inorganic nanoparticles, and wherein the condensed layer is disposed between the core and the nanoparticle layer;
an inorganic second shell component surrounding the first shell component, wherein the second shell component surrounds the nanoparticle layer;
wherein the precursor comprises at least one compound from the group consisting of Formula (I), Formula (II), and a mixture thereof,
wherein Formula (I) is $(M^vO_zY_n)_w$,
wherein Formula (II) is $(M^vO_zY_nR^1_p)_w$,
wherein for Formula (I), Formula (II), or the mixture thereof:
each M is independently selected from the group consisting of silicon, titanium, and aluminum,
v is the valence number of M and is 3 or 4,
z is from 0.5 to 1.6,
each Y is independently selected from —OH, —OR$^2$, halogen,

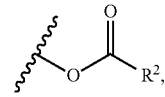

—NH$_2$, —NHR$^2$, —N(R$^2$)$_2$, and

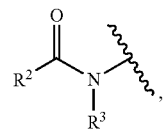

wherein R$^2$ is a C$_1$ to C$_{20}$ alkyl, C$_1$ to C$_{20}$ alkylene, C$_6$ to C$_{22}$ aryl, or a 5-12 membered heteroaryl, wherein the heteroaryl comprises from 1 to 3 ring heteroatoms selected from O, N, and S,
wherein R$^3$ is a H, C$_1$ to C$_{20}$ alkyl, C$_1$ to C$_{20}$ alkylene, C$_6$ to C$_{22}$ aryl, or a 5-12 membered heteroaryl, wherein the heteroaryl comprises from 1 to 3 ring heteroatoms selected from O, N, and S,
w is from 2 to 2000;
wherein for Formula (I),
n is from 0.7 to (v−1); and
wherein for Formula (II),
n is from 0 to (v−1),
each R$^1$ is independently selected from the group consisting of: a C$_1$ to C$_{30}$ alkyl; a C$_1$ to C$_{30}$ alkylene; a C$_1$ to C$_{30}$ alkyl substituted with a member selected from the group consisting of a halogen, —OCF$_3$, —NO$_2$, —CN, —NC, —OH, —OCN, —NCO, alkoxy, epoxy, amino, mercapto, acryloyl, —CO$_2$H, —C(O)-alkyl, —C(O)O-aryl, and —C(O)O-heteroaryl; and a C$_1$ to C$_{30}$ alkylene substituted with a member selected from the group consisting of a halogen, —OCF$_3$, —NO$_2$, —CN, —NC, —OH, —OCN, —NCO, alkoxy, epoxy, amino, mercapto, acryloyl, —C(O)OH, —C(O)O-alkyl, —C(O)O-aryl, and —C(O)O-heteroaryl; and
p is a number that is greater than zero and is up to pmax, wherein $p$ max=60/[9*$Mw(R^1)$+8], wherein Mw(R$^1$) is the molecular weight of the R$^1$ group.

BRIEF DESCRIPTION OF THE DRAWINGS

The figures herein are illustrative in nature and are not intended to be limiting.

FIG. 1 shows a schematic illustration of the method of making capsules with a first shell component, prepared with a hydrophobic core.

DETAILED DESCRIPTION OF THE INVENTION

Figure 3:
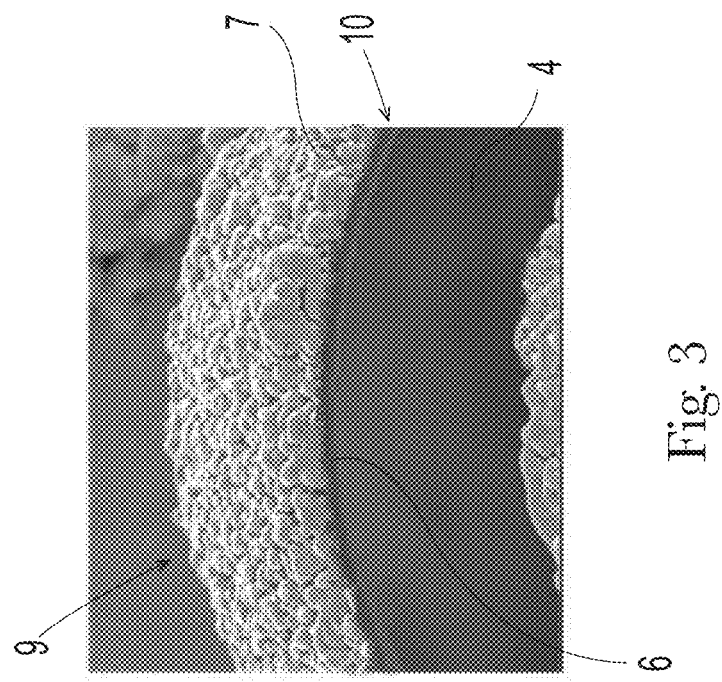
FIG. 3 is a scanning electron microscopy image of a capsule.

The present disclosure relates to antiperspirant and deodorant compositions that include a population of capsules that contain perfume raw materials. The shells of the capsules contain inorganic materials, the selection of which results in improved mechanical properties and low permeability.

For example, it has been found that the capsules of the present disclosure work surprisingly well in controlling the leakage of the perfume raw materials in the presently disclosed compositions, resulting in relatively low and consistent perfume leakage. Without wishing to be bound by theory, it is believed that the leakage of perfume raw materials is driven by radically different mechanisms for shell containing highly crosslinked inorganic materials compared to shell containing organic polymeric materials. Specifically, the diffusion of small molecules such as perfume raw materials ("PRMs") across a homogenous organic polymeric shell is similar to the diffusion mechanism across a homogeneous polymeric membrane. In this case, the permeability of the polymeric membrane for a given solute depends both on the polymer free volume (impacted by degree of crystallinity and cross-linked density) as well as the relative solubility of the solute for the polymer. Since different PRMs will have different ranges of relevant physical and chemical properties (e.g., molecular weight and polarity), the rates of diffusion are not uniform for a given set of PRMs when the physical and chemical properties are also not uniform.

On the other hand, it is believed that diffusion of small molecules across a highly crosslinked inorganic shell occurs primarily through the microchannels formed by the percolating network of micropores present in the shell. Such highly crosslinked inorganic shell can be obtained by using a second shell component in combination with a first shell component, as disclosed with the present disclosure. In this case, it is believed that the permeability of the inorganic shell primarily depends on the number, density, and dimensions of the microchannels that are effectively connecting the core and continuous phases, which can result in the PRM leakage rates being relatively uniform or consistent with respect to each other, as well as being relatively low.

Additionally, it is believed that these capsules of the present disclosure provide a suitable barrier against the aggressive chemistry found in deodorant and antiperspirant compositions. The solvents used in deodorant products are often excellent solvents for perfume materials; therefore, the perfume can be extracted from the capsule thus losing the expected benefit. Additionally, antiperspirant actives are highly acidic, and can cause instability for susceptible materials. The present invention shows a stable benefit in the presence of solvent capable of dissolving perfume. The present invention also shows a stable benefit in the presence of an antiperspirant active.

Because the various PRMs leak from the disclosed capsules in the disclosed compositions at relatively consistent rates, it is further believed that the intended character of the perfume is maintained, leading to a more satisfactory and consistent olfactory performance.

The components, compositions, and related processes are described in more detail below.

As used herein, the articles "a" and "an" when used in a claim, are understood to mean one or more of what is claimed or described. As used herein, the terms "include," "includes," and "including" are meant to be non-limiting.

The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein the phrase "antiperspirant and deodorant compositions" refers to compositions, including but not limited to, roll-ons, gels, clear gels, solid sticks, aerosols, and soft-solid sticks. For example, the antiperspirant or deodorant composition may be a composition such as a soft-solid deodorant, soft-solid antiperspirant, an invisible solid deodorant, an invisible solid antiperspirant, aerosol antiperspirant, fluid antiperspirant, body powder, or body spray. Such antiperspirant and deodorant compositions include compositions that are applied to at least a portion of the body, and which are used to combat body odor. "Soft solid" refers to a composition with a static yield stress of about 200 Pa to about 1,500 Pa after dispensing.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Antiperspirant and Deodorant Compositions

The present disclosure relates to antiperspirant and deodorant compositions. Antiperspirant and deodorant compositions can be formulated in many forms. Deodorant compositions control body odor and optionally can include an antiperspirant active. For example, a deodorant or antiperspirant composition can be, without limitation, a roll-on product, a body spray, a stick including soft solid sticks and invisible solids, or an aerosol. Each of the deodorant compositions described below can include perfume materials as described herein. Each of the deodorant compositions described below can further include an antiperspirant active and thus be described as a deodorant and/or an antiperspirant composition.

A. Roll-On, Clear Gel, and Glycol Deodorant Stick

A roll-on deodorant composition can comprise, for example, water, emollient, solubilizer, deodorant actives, antioxidants, preservatives, antiperspirant actives, or combinations thereof. A clear gel deodorant composition can comprise, for example, water, emollient, solubilizer, deodorant actives, antioxidants, preservatives, ethanol (alcohol denatured), odor entrappers, buffering agents, antiperspirant actives, or combinations thereof.

Water

The roll-on composition can include water. Water can be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the deodorant composition. In some embodiments, the composition may comprise at least about 5% water, or at least about 70% water.

Emollients

Roll-on compositions can comprise an emollient system including at least one emollient, but it could also be a combination of emollients. Suitable emollients are often liquid under ambient conditions. Depending on the type of product form desired, concentrations of the emollient(s) in the deodorant compositions can range from about 1% to about 95%, from about 5% to about 95%, from about 15% to about 75%, from about 1% to about 10%, from about 15% to about 45%, or from about 1% to about 30%, by weight of the deodorant composition.

Emollients suitable for use in the roll-on compositions include, but are not limited to, propylene glycol, polypropylene glycol (like dipropylene glycol, tripropylene glycol, etc.), diethylene glycol, triethylene glycol, PEG-4, PEG-8, 1,2 pentanediol, 1,2 hexanediol, hexylene glycol, glycerin, C2 to C20 monohydric alcohols, C2 to C40 dihydric orpolyhydric alcohols, alkyl ethers of polyhydric and monohydric alcohols, volatile silicone emollients such as cyclopentasiloxane, nonvolatile silicone emollients such as dimethicone, mineral oils, polydecenes, petrolatum, and combinations thereof. One example of a suitable emollient comprises PPG-15 stearyl ether. Other examples of suitable emollients include dipropylene glycol and propylene glycol.

Deodorant Actives

Suitable deodorant actives can include any topical material that is known or otherwise effective in preventing or eliminating malodor associated with perspiration. Suitable deodorant actives may be selected from the group consisting of antimicrobial agents (e.g., bacteriocides, fungicides), malodor-absorbing material, and combinations thereof. For example, antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, piroctone olamine, heavy metal salts of citrate, salicylate, and piroctose, especially zinc salts, and acids thereof, heavy metal salts of pyrithione, especially zinc pyrithione, zinc phenolsulfate, farnesol, magnesium salts, including magnesium hydroxide, magnesium oxide, magnesium carbonate and combinations thereof. The concentration of the optional deodorant active may range from about 0.001%, from about 0.01%, of from about 0.1%, by weight of the composition to about 20%, to about 10%, to about 5%, or to about 1%, by weight of the composition.

Odor Entrappers

The composition can include an odor entrapper. Suitable odor entrappers for use herein include, for example, solubilized, water-soluble, uncomplexed cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many perfume molecules can fit into the cavity.

Cyclodextrin molecules are described in U.S. Pat. Nos. 5,714,137, and 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the composition.

Buffering Agent

The composition can include a buffering agent which may be alkaline, acidic or neutral. The buffer can be used in the composition for maintaining the desired pH. The composition may have a pH from about 3 to about 10, from about 4 to about 9, from about 5 to about 8, from about 6 to about 7, or it may have a pH of about 6.5. One unique feature of the polyvinyl amine malodor control polymers is its ability to maintain active nitrogen sites at high pH levels which can help enhance the antibacterial effect which comes, at least in part, from the nitrogen sites.

Suitable buffering agents include, for example, hydrochloric acid, sodium hydroxide, potassium hydroxide, and combinations thereof.

The compositions can contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

Solubilizer

The composition can contain a solubilizer. A suitable solubilizer can be, for example, a surfactant, such as a no-foaming or low-foaming surfactant. Suitable surfactants are nonionic surfactants, cationic surfactants, amphoteric surfactants, zwitterionic surfactants, and mixtures thereof.

Suitable solubilizers include, for example, hydrogenated castor oil, polyoxyethylene 2 stearyl ether, polyoxyethylene 20 stearyl ether, and combinations thereof. One suitable hydrogenated castor oil that may be used in the present composition is polyoxyethylene hydrogenated castor oil.

When the solubilizing agent is present, it is typically present at a level of from about 0.01% to about 5%, alternatively from about 0.01% to about 3%, alternatively from about 0.05% to about 1%, alternatively from about 0.01% to about 0.05%, by weight of the composition.

Preservatives

The composition can include a preservative. The preservative is included in an amount sufficient to prevent spoilage or prevent growth of inadvertently added microorganisms for a specific period of time, but not sufficient enough to contribute to the odor neutralizing performance of the composition. In other words, the preservative is not being used as the antimicrobial compound to kill microorganisms on the surface onto which the composition is deposited in order to eliminate odors produced by microorganisms. Instead, it is being used to prevent spoilage of the composition in order to increase shelf-life.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diaol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Index; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N''-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hills America; formal-dehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative can range from about 0.0001% to about 0.5%, alternatively from about 0.0002% to about 0.2%, alternatively from about 0.0003% to about 0.1%, by weight of the composition.

Ethanol

The antiperspirant and/or deodorant composition may comprise ethanol. In some embodiments, the composition may comprise from about 5% to about 15% ethanol, or from about 5% to about 10% ethanol.

Glycol

Aqueous deodorant formulations may optionally contain glycols. When used as a carrier, glycols are known in the art to promote a hostile environment for bacterial growth. Glycol materials may include but are not limited to dipropylene glycol, propylene glycol, 1,3 Propanediol, butylene glycol, tripropylene glycol, hexylene glycol, 1,2 hexane diol, PPG-10 butantediol, and polyethylene glycol.

In some embodiments, deodorant sticks may comprise at least about 25% of one or more glycols, by weight of the composition. In some embodiments, deodorant sticks may comprise sodium stearate or stearic acid as a structurant. See Example 6 below. In some embodiments, the stick composition may comprise from about 25% to about 75% glycol as a primary carrier, in addition to comprising the components described above, such as deodorant and/or antiperspirant actives, perfumes, and water.

B. Body Spray

A body spray can contain, for example, a carrier, perfume, a deodorant active, odor entrappers, propellant, or combinations thereof. The body spray compositions can be applied as a liquid.

Carrier

A carrier suitable for use in a body spray can include, water, alcohol, or combinations thereof. The carrier may be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the composition. Some embodiments may comprise at least about 30% of a short-chain alcohol, such as ethanol. A suitable example of an alcohol can include ethanol.

Propellant

The compositions described herein can include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoro-ethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42%, or any combination thereof, by weight of the total fill of materials stored within the container.

C. Invisible Solid

Invisible solid deodorant compositions as described herein can contain a primary structurant, an antiperspirant active, deodorant active, a perfume, and additional chassis ingredient(s). The deodorant composition can further comprise other optional ingredient(s). The compositions can be in the form of a solid stick. The compositions can have a product hardness of about 600 gram force or more. The compositions may be free of dipropylene glycol, added water, castor wax, or any combination thereof. The antiperspirant composition may be anhydrous. The antiperspirant composition may be free of added water.

Hardness

The invisible solid can have a product hardness of least about 600 gram·force, more specifically from about 600 gram·force to about 5,000 gram·force, still more specifically from about 750 gram·force to about 2,000 gram·force, and yet more specifically from about 800 gram·force to about 1,400 gram·force.

The term "product hardness" or "hardness" as used herein is a reflection of how much force is required to move a penetration cone a specified distance and at a controlled rate into an antiperspirant composition under the test conditions described herein below. Higher values represent harder product, and lower values represent softer product. These values are measured at 27° C. 15% relative humidity, using a TA-XT2 Texture Analyzer, available from Texture Technology Corp., Scarsdale, N.Y., U.S.A. The product hardness value as used herein represents the peak force required to move a standard 45-degree angle penetration cone through the composition for a distance of 10 mm at a speed of 2 mm/second. The standard cone is available from Texture Technology Corp., as part number TA-15, and has a total cone length of about 24.7 mm, angled cone length of about 18.3 mm, and a maximum diameter of the angled surface of the cone of about 15.5 mm. The cone is a smooth, stainless steel construction and weighs about 17.8 grams.

Primary Structurants

The invisible solid can comprise a suitable concentration of a primary structurant to help provide the deodorant or antiperspirant with the desired viscosity, rheology, texture and/or product hardness, or to otherwise help suspend any dispersed solids or liquids within the composition.

The term "solid structurant" as used herein means any material known or otherwise effective in providing suspending, gelling, viscosifying, solidifying, and/or thickening properties to the composition or which otherwise provide structure to the final product form. These solid structurants include gelling agents, and polymeric or non-poly meric or inorganic thickening or viscosifying agents. Such materials will typically be solids under ambient conditions and include organic solids, crystalline or other gellants, inorganic particulates such as clays or silicas, or combinations thereof.

The concentration and type of solid structurant selected for use in the deodorant and antiperspirant compositions will vary depending upon the desired product hardness, rheology, and/or other related product characteristics. For most structurants suitable for use herein, the total structurant concentration ranges from about 5% to about 35%, more typically from about 10% to about 30%, or from about 7% to about 20%, by weight of the composition.

Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fischer-Tropsch waxes, and microcrystalline wax; polyethylenes with molecular weight of 200 to 1000 daltons; solid triglycerides; behenyl alcohol, or combinations thereof.

Other non-limiting examples of primary structurants suitable for use herein are described in U.S. Pat. Nos. 5,976,514 and 5,891,424, the descriptions of which are incorporated herein by reference.

Antiperspirant Active

The deodorant stick compositions can comprise a particulate antiperspirant active suitable for application to human skin. The concentration of antiperspirant active in the composition should be sufficient to provide the desired perspiration wetness and odor control from the antiperspirant stick formulation selected.

The deodorant stick compositions can comprise an antiperspirant active at concentrations of from about 0.5% to about 60%, and more specifically from about 5% to about 35%, by weight of the composition. These weight percentages are calculated on an anhydrous metal salt basis exclusive of water and any complexing agents such as, for example, glycine, and glycine salts. The antiperspirant active as formulated in the composition can be in the form of dispersed particulate solids having an average particle size or equivalent diameter of less than about 100 microns, more specifically less than about 20 microns, and even more specifically less than about microns.

The antiperspirant active for use in the anhydrous antiperspirant compositions of the present invention can include any compound, composition or other material having antiperspirant activity. More specifically, the antiperspirant actives may include astringent metallic salts, especially inorganic and organic salts of aluminum, zirconium and zinc, as well as mixtures thereof. Even more specifically, the antiperspirant actives may include aluminum-containing and/or zirconium-containing salts or materials, such as, for example, aluminum halides, aluminum chlorohydrate, aluminum hydroxy halides, zirconyl oxyhalides, zirconyl hydroxyhalides, and mixtures thereof.

Aluminum salts for use in the anhydrous antiperspirant stick compositions include those that conform to the formula:

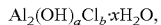

$$Al_2(OH)_aCl_b \cdot xH_2O,$$

wherein a is from about 2 to about 5;
the sum of a and b is about 6;
x is from about 1 to about 6; and
a, b, and x may have non-integer values.

More specifically, aluminum chlorohydroxides referred to as "5/6 basic chlorohydroxide" can be used, wherein a=5, and "2/3 basic chlorohydroxide", wherein a=4.

Processes for preparing aluminum salts are disclosed in U.S. Pat. Nos. 3,887,692; 3,904,741; 4,359,456; and British Patent Specification 2,048,229, the disclosures of which are incorporated herein by reference for the purpose of describing processes for preparing aluminum salts.

Mixtures of aluminum salts are described in British Patent Specification 1,347,950, which description is also incorporated herein by reference.

Zirconium salts for use in the anhydrous antiperspirant stick compositions include those which conform to the formula:

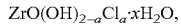

$$ZrO(OH)_{2-a}Cl_a \cdot xH_2O,$$

wherein a is from about 1.5 to about 1.87;
x is from about 1 to about 7; and
a and x may both have non-integer values.

These zirconium salts are described in Belgian Patent 825,146, Schmitz, issued Aug. 4, 1975, which description is incorporated herein by reference. Zirconium salts that additionally contain aluminum and glycine, commonly known as "ZAG complexes," are believed to be especially beneficial. These ZAG complexes contain aluminum chlorohydroxide and zirconyl hydroxy chloride conforming to the above-described formulas. Such ZAG complexes are described in U.S. Pat. No. 3,792,068; Great Britain Patent Application 2,144,992; and U.S. Pat. No. 4,120,948, disclosures of which are incorporated herein by reference for the limited purpose of describing ZAG complexes.

Also suitable for use herein are enhanced efficacy aluminum-zirconium chlorohydrex-amino acid which typically has the empirical formula $AlnZr(OH)_{[3n+4-m(n+1)]}(Cl)_{[m(n+1)]} \cdot AAq$ where n is 2.0 to 10.0, preferably 3.0 to 8.0; m is about 0.48 to about 1.11 (which corresponds to M:Cl approximately equal to 2.1-0.9), preferably about 0.56 to about 0.83 (which corresponds to M:Cl approximately equal to 1.8-1.2); q is about 0.8 to about 4.0, preferably about 1.0 to 2.0; and AA is an amino acid such as glycine, alanine, valine, serine, leucine, isoleucine, β-alanine, cysteine, β-amino-n-butyric acid, or γ-amino-n-butyric acid, preferably glycine. These salts also generally have some water of hydration associated with them, typically on the order of 1 to 5 moles per mole of salt (typically, about 1% to about 16%, more typically about 4% to about 13% by weight). These salts are generally referred to as aluminum-zirconium trichlorohydrex or tetrachlorohydrex when the Al:Zr ratio is between 2 and 6 and as aluminum-zirconium pentachlorohydrex or octachlorohydrex when the Al:Zr ratio is between 6 and 10. The term "aluminum-zirconium chlorohydrex" is intended to embrace all of these forms. The preferred aluminum-zirconium salt is aluminum-zirconium chlorohydrex-glycine. Additional examples of suitable high efficacy antiperspirant actives can include Aluminum Zirconium Pentachlorohydrex Glycine, Aluminum Zirconium Octachlorohydrex Glycine, or a combination thereof. These high efficacy actives are more fully described in U.S. App. Pub. No. 2007/0003499 by Shen et al. filed Jun. 30, 2005.

Additional Chassis Ingredients

Additional Structurant

The deodorant or antiperspirant composition can further comprise an additional structurant. The additional structurant may be present in an amount from 1% to about 10%, by weight of the composition. The additional structurant(s) will likely be present at an amount less than the primary structurant.

Non-limiting examples of suitable additional structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; and solid triglycerides; behenyl alcohol, or combinations thereof.

Other non-limiting examples of additional structurants suitable for use herein are described in U.S. Pat. Nos. 5,976,514 and 5,891,424.

Solvent

The deodorant composition can comprise a solvent at concentrations ranging from about 20% to about 80%, and more specifically from about 30% to about 70%, by weight of the composition. The solvent can be a volatile silicone which may be cyclic or linear.

"Volatile silicone" as used herein refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976), which descriptions are incorporated herein by reference.

The volatile silicone can be a cyclic silicone having from 3 to 7, and more specifically from 5 to 6, silicon atoms, and still more specifically 5, like cyclopentasiloxane. These cyclic silicone materials will generally have viscosities of less than about 10 centistokes at 25° C.

Linear volatile silicone materials suitable for use in the deodorant compositions include those represented by the formula:

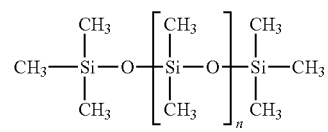

wherein n is from 1 to 7, and more specifically from 2 to 3. These linear silicone materials will generally have viscosities of less than about 5 centistokes at 25° C.

Specific examples of volatile silicone solvents suitable for use in the deodorant and antiperspirant compositions include, but are not limited to, Cyclomethicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

Non-Volatile Organic Fluids

Non-volatile organic fluids may be present, for example, in an amount of about 15% or less, by weight of the composition.

Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate, and isobutyl stearate.

Other Optional Ingredients

The anhydrous deodorant compositions can further comprise any optional material that is known for use in antiperspirant and deodorant compositions or other personal care products, or which is otherwise suitable for topical application to human skin.

One example of optional materials are clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Talc, if used at higher levels can produce a significant amount of white residue which has been found to be a consumer negative for product acceptance. Therefore it is best to limit the composition to less than 10%, less than about 8%, less than about 6%, or less than about 3%, by weight of the composition.

Nonlimiting examples of other optional materials include emulsifiers, distributing agents, antimicrobials, pharmaceutical or other topical active, preservatives, surfactants, and so forth. Examples of such optional materials are described in U.S. Pat. Nos. 4,049,792; 5,019,375; and 5,429,816; which descriptions are incorporated herein by reference.

Some solid stick emulsions may have the structurants disclosed in this section. See the Solid Stick emulsions of Example 8.

D. Soft Solid

Soft solid deodorant compositions can comprise volatile silicone, antiperspirant active, gellant, residue masking material, or combinations thereof. In addition, soft solids generally have a hardness value after dispensing of about 500 gram force or less. In some embodiments, the composition may be substantially free of water, or free of water.

Volatile Silicone Solvent

The soft solid can comprise a volatile silicone solvent at concentrations ranging from about 20% to about 80%, preferably from about 30% to about 70%, more preferably from about 45% to about 70%, by weight of the composition. The volatile silicone of the solvent may be cyclic or linear.

"Volatile silicone" as used herein refers to those silicone materials which have measurable vapor pressure under ambient conditions. Nonlimiting examples of suitable volatile silicones are described in Todd et al., "Volatile Silicone Fluids for Cosmetics", Cosmetics and Toiletries, 91:27-32 (1976), which descriptions are incorporated herein by reference. Preferred volatile silicone materials are those having from about 3 to about 7, preferably from about 4 to about 5, silicon atoms.

Cyclic volatile silicones are preferred for use in the deodorant and antiperspirant compositions herein, and include those represented by the formula:

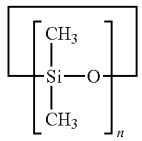

wherein n is from about 3 to about 7, preferably from about 4 to about 5, most preferably 5. These cyclic silicone materials will generally have viscosities of less than about 10 centistokes at 25° C.

Linear volatile silicone materials suitable for use in the deodorant and antiperspirant compositions include those represented by the formula:

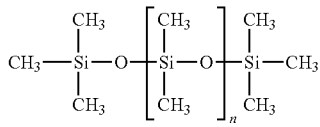

wherein n is from about 1 to about 7, preferably from about 2 to about 3. These linear silicone materials will generally have viscosities of less than about 5 centistokes at 25° C.

Specific examples of volatile silicone solvents suitable for use in the deodorant and antiperspirant compositions include, but are not limited to, Cyclomethicone D-5 (commercially available from G. E. Silicones), Dow Corning 344, Dow Corning 345 and Dow Corning 200 (commercially available from Dow Corning Corp.), GE 7207 and 7158 (commercially available from General Electric Co.) and SWS-03314 (commercially available from SWS Silicones Corp.).

Gellant Material

The soft solid can include a gellant material comprising fatty alcohols having from about 20 to about 60 carbon atoms, or combinations thereof, at concentrations ranging from about 0.1% to about 8% by weight of the composition. The gellant material, when combined with the volatile silicone solvent described hereinbefore, provides the composition with a physically stable structure within which the particulate antiperspirant materials are dispersed, and maintained as such over an extended period of time.

Specifically, the gellant material can comprise saturated or unsaturated, substituted or unsubstituted, fatty alcohols or mixtures of fatty alcohols having from about 20 to about 60 carbons atoms, preferably from about 20 to about 40 carbon atoms. Preferred are combinations of the fatty alcohols. The fatty alcohol gellants are preferably saturated, unsubstituted monohydric alcohols or combinations thereof, which have a melting point of at less than about 110° C., more preferably from about 60° to about 110° C., even more preferably between about 100° C. and 110° C.

It has been found that this fatty alcohol-based gellant material, when combined with volatile silicone solvents provides a stable structure for maintaining a dispersion of particulate antiperspirant material in a topical formulation without the necessity of using conventional particulate thickening agents. This gellant material is especially useful in maintaining the physical stability of particulate dispersions containing higher concentrations of volatile silicone solvents.

It was also found that penetration force values for the deodorant and antiperspirant compositions can be controlled by adjusting total fatty alcohol concentrations. In controlling penetration force values in this manner, there is no longer a need to use organic solvents or thickening agents to control penetration force values, which solvents or thickening agents often add cost to the formulation, introduce additional compatibility issues, and often contribute undesirable cosmetics such as prolonged stickiness, difficulty in ease of spreading, increased dry-down times and reduced dry feel after application.

Specific concentrations of the gellant materials can be selected according to the desired penetration force value. For roll-on formulations having a penetration force value of from about 20 gram·force to about 100 gram·force, gellant material concentrations preferably range from about 0.1% to about 3%, preferably from about 1.5% to about 3%, by weight of the antiperspirant composition. For other cream formulations, including those formulations suitable for use in cream applicator devices, which have a penetration force value of from about 100 gram·force to about 500 gram·force, gellant material concentrations preferably range from about 3% to about 8%, preferably from about 3% to about 6%, by weight of the antiperspirant composition.

Specific examples of fatty alcohol gellants for use in the deodorant and antiperspirant compositions that are commercially available include, but are not limited to, Unilin® 425, Unilin® 350, Unilin®550 and Unilin® 700 (supplied by Petrolite)

Residue Masking Material

The soft solid compositions can further comprise a non-volatile emollient as a residue masking material. Such materials and their use in deodorant and antiperspirant compositions are well known in the art, and any such material may be incorporated into the composition of the present invention, provided that such optional material is compatible with the essential elements of the composition, or does not unduly impair product performance or cosmetics.

Concentrations of the optional residue masking material can range from about 0.1% to about 40%, preferably from about 1% to about 10%, by weight of the composition. These optional materials can be liquid at ambient temperatures, and can be nonvolatile. The term "nonvolatile" as used in this context refers to materials which have a boiling point under atmospheric pressure of at least about 200° C. Non-limiting examples of suitable residue masking materials for use in the deodorant and antiperspirant compositions include butyl stearate, diisopropyl adipate, petrolatum, nonvolatile silicones, octyldodecanol, phenyl trimethicone, isopropyl myristate, C12-15 ethanol benzoates and PPG-14 Butyl Ether. Residue masking materials are described, for example, in U.S. Pat. No. 4,985,238, which description is incorporated herein by reference.

Other Materials

The soft solid compositions can further comprise one, or more, other materials which modify the physical characteristics of the compositions or serve as additional "active" components when deposited on the skin. Many such materials are known in the deodorant and antiperspirant art and can be used in the compositions herein, provided that such optional materials are compatible with the essential materials described herein, or do not otherwise unduly impair product performance.

Non limiting examples of materials can include active components such as bacteriostats and fungiostats, and "non-active" components such as colorants, perfumes, cosmetic powders, emulsifiers, chelants, distributing agents, preservatives, and wash-off aids. Examples of such optional materials are described in U.S. Pat. No. 4,049,792; Canadian Patent 1,164,347; U.S. Pat. Nos. 5,019,375; and 5,429,816; which descriptions are incorporated herein by reference.

E. Aerosol

An aerosol composition can comprise a concentrate, a propellant, or a combination thereof. Alcohol is a predominant component of the concentrates provided herein. Useful alcohols include $C_1$-$C_3$ alcohols, with the preferred alcohol being ethanol. In certain examples, the alcohol is employed at a concentration level of from at least about 40%, 50% or 55% to about 80%, by weight of the concentrate.

An antiperspirant active may be dissolved in the alcohol at a level of from about 1% to about 15%, by weight of the concentrate. Various antiperspirant actives can be employed, including, for example, aluminum chloride, aluminum chlorohydrate, aluminum chlorohydrex, aluminum chlorohydrex PG, aluminum chlorohydrex PEG, aluminum dichlorohydrate, aluminum dichlorohydrex PG, aluminum dichlorohydrex PEG, aluminum sesquichlorohydrate, aluminum sesquichlorohydrex PG, aluminum sesquichlorohydrex PEG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrex GLY, and aluminum zirconium trichlorohydrex GLY. In one example, aluminum chlorohydrex PG is the chosen antiperspirant active.

The deodorant or antiperspirant concentrates can also include an oil or a mixture of two or more oils. Useful oils include, for example, volatile silicone oils and non-volatile organic oils. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976). The volatile silicone can be a cyclic silicone having from at least about 3 silicone atoms or from at least about 5 silicone atoms but no more than about 7 silicone atoms or no more than about 6 silicone atoms. For example, volatile silicones can be used which conform to the formula:

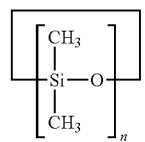

wherein n is from about 3 or from about 5 but no more than about 7 or no more than about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); MASIL SF-V (available from Mazer) and combinations thereof. Suitable volatile silicone oils can also include linear silicone oils such as, for example, DC200 (1 cSt), DC200 (0.65 cSt), and DC2-1184, all of which are available from Dow Corning Corp. In certain examples, the volatile silicone oil can have a viscosity of less than 10 centistokes at 25° C.

Non-volatile organic, emollient oils can also be employed. A representative, non-limiting list of emollient oils includes CETIOL CC (dicaprylyl carbonate), CETIOL OE (dicaprylyl ether), CETIOL S (diethylhexylcyclohexane), and CETIOL B (dibutyl adipate), all of which are available from Cognis, and LEXFEEL 7 (neopentyl glycol diheptanoate) from Index. In certain examples, the organic emollient oils have a viscosity of less than 50 centistokes at 25° C. The term "organic emollient oil" as used herein means silicon-free emollient oils that are liquid at 25° C., and that are safe and light to skin and can be miscible with volatile silicone oils (as described above) and the antiperspirant active-alcohol solution in the concentration ranges described below.

The oil or mixture of oils is generally included in the concentrate formulas at a level of from about 5% to about 45%, by weight of the concentrate. The viscosity ranges noted above in connection with the different classes of oil can facilitate desired spray rates and patterns, and can help minimize nozzle clogging. To provide desired skin feel, minimal nozzle clogging, and good concentrate stability, the ratio of alcohol to volatile silicone oil is preferably greater than 1.0, 1.35, or 1.5. And in examples having both a volatile silicone oil and an organic emollient oil, the ratio of alcohol to total oil is preferably greater than or equal to about 0.90. The oils in certain examples are miscible with the alcohol and antiperspirant active solution. Although various levels of miscibility are acceptable, the oils are preferably miscible enough with the alcohol and antiperspirant active solution to yield a concentrate having a clear appearance.

The deodorant compositions can also include residue-masking agents and propellants as discussed above.

The compositions may comprise a population of capsules. The capsules contain perfume and may provide aromatic/freshness benefits at various touchpoints. The compositions may also comprise an antiperspirant active to reduce wetness and/or deodorant actives to help control malodor.

Population of Capsules

The antiperspirant and deodorant compositions of the present disclosure further include a population of capsules. As described in more detail below, the capsules may include a core surrounded by substantially inorganic shell.

The capsules may be present in the composition in an amount that is from about 0.05% to about 20%, or from about 0.05% to about 10%, or from about 0.1% to about 5%, or from about 0.2% to about 2%, by weight of the composition. The composition may comprise a sufficient amount of capsules to provide from about 0.05% to about 10%, or from about 0.1% to about 5%, or from about 0.1% to about 2%, by weight of the composition, of perfume raw materials to the composition. When discussing herein the amount or weight percentage of the capsules, it is meant the sum of the shell material and the core material.

The capsules can have a mean shell thickness of 10 nm to 10,000 nm, preferably 170 nm to 1000 nm, more preferably 300 nm to 500 nm.

In certain embodiments, the mean volume weighted diameter of the capsule is between 1 and 200 micrometers, preferably between 1 and 10 micrometers, even more preferably between 2 and 8 micrometers. In another embodiment, the shell thickness is between 1 and 10000 nm, 1-1000 nm, 10-200 nm. In a further embodiment, the capsules have a mean volume weighted diameter between 1 and 10 micrometers and a shell thickness between 1 and 200 nm. It has been found, that capsules with a mean volume weighted diameter between 1 and 10 micrometers and a shell thickness between 1 and 200 nm have a higher Fracture strength Without intending to be bound by theory, it is believed that the higher Fracture strength provides a better survivability during use of a product, wherein said use can cause premature rupture of mechanically weak capsules due to the mechanical constraints during use.

Capsules having a mean volume weighted diameter between 1 and 10 micrometers and a shell thickness between 10 and 200 nm offer resistance to mechanical constraints only when made with a certain selection of the silica precursor used. In some embodiments, said precursor has a molecular weight between 2 and 5 kDa, even more preferably a molecular weight between 2.5 and 4 kDa. In addition, the concentration of the precursor needs to be carefully selected, wherein said concentration is between 20 and 60 w %, preferably between 40 and 60 w % of the oil phase used during the encapsulation.

Without intending to be bound by theory, it is believed that higher molecular weight precursors have a much slower migration time from the oil phase into the water phase. The slower migration time is believed to arise from the combination of 3 phenomenon: diffusion, partitioning, and reaction kinetics. This phenomenon is important in the context of small sized capsules, due to the fact that the overall surface area between oil and water in the system increases as the capsule diameter decreases. A higher surface area leads to higher migration of the precursor from the oil phase to the water phase, which in turn reduces the yield of polymerization at the interface. Therefore, the higher molecular weight precursor are needed to mitigate the effects brought by an in increase in surface area, and to obtain capsules according to this invention.

In some embodiments, the capsules can have a mean volume weighted capsule diameter of 0.1 micrometers to 300 micrometers, 10 micrometers to 200 micrometers, or 10 micrometers to 50 micrometers. It has been advantageously found that large capsules (e.g., mean diameter of 10 μm or greater) can be provided in accordance with embodiments herein without sacrificing the stability of the capsules as a whole and/or while maintaining good fracture strength.

It has surprisingly been found that in addition to the inorganic shell, the volumetric core-shell ratio can play an important role to ensure the physical integrity of the capsules. Shells that are too thin vs. the overall size of the capsule (core:shell ratio >98:2) tend to suffer from a lack of self-integrity. On the other hand, shells that are extremely thick vs. the diameter of the capsule (core:shell ratio <80:20) tend to have higher shell permeability in a surfactant-rich matrix. While one might intuitively think that a thick shell leads to lower shell permeability (since this parameter impacts the mean diffusion path of the active across the shell), it has surprisingly been found that the capsules of this invention that have a shell with a thickness above a threshold have higher shell permeability. It is believed that this upper threshold is, in part, dependent on the capsule diameter.

The capsules may have a mean effective volumetric core-shell ratio of 50:50 to 99:1, preferably from 60:40 to 99:1, preferably 70:30 to 98:2, more preferably 80:20 to 96:4.

It may be desirable to have particular combinations of these capsule characteristics. For example, the capsules can have a mean effective volumetric core-shell ratio of about 99:1 to about 50:50, and have a mean volume weighted capsule diameter of about 0.1 μm to about 200 μm, and a mean shell thickness of about 10 nm to about 10,000 nm. The capsules can have a mean effective volumetric core-shell ratio of about 99:1 to about 50:50, and have a mean volume weighted capsule diameter of about 10 μm to about 200 μm, and a mean shell thickness of about 170 nm to about 10,000 nm. The capsules can have a mean effective volumetric core-shell ratio of about 98:2 to about 70:30, and have a mean volume weighted capsule diameter of about 10 μm to about 100 μm, and a mean shell thickness of about 300 nm to about 1000 nm.

Methods according to the present disclosure can produce capsule having a low coefficient of variation of capsule diameter. Control over the distribution of size of the capsules can beneficially allow for the population to have improved and more uniform fracture strength. A population of capsules can have a coefficient of variation of capsule diameter of 40% or less, preferably 30% or less, more preferably 20% or less.

For capsules containing a core material to perform and be cost effective in consumer good applications, such as an antiperspirant or deodorant, they should: i) be resistant to core diffusion during the shelf life (e.g., low leakage or permeability); ii) have ability to deposit on the targeted surface during application, and iii) be able to release the core material by mechanical shell rupture at the right time and place to provide the intended benefit for the end consumer.

The capsules described herein can have an average fracture strength of 0.1 MPa to 10 MPa, preferably 0.25 MPa to 5 MPa, more preferably 0.25 MPa to 3 MPa. Fully inorganic capsules have traditionally had poor fracture strength, whereas for the capsules described herein, the fracture strength of the capsules can be greater than 0.25 MPa, providing for improved stability and a triggered release of the benefit agent upon a designated amount of rupture stress.

It is believed that permeability, as measured by the Permeability Test Method described below, correlates to the porosity of the capsule shells. The capsules or populations of capsules may have a permeability as measured by the Permeability Test Method of about 0.01% to about 80%, preferably about 0.01% to about 60%, even more preferably about 0.01% to 40%.

i. Core

The capsules include a core. The core may be oil-based, or the core may be aqueous. Preferably, the core is oil-based. The core may be a liquid at the temperature at which it is utilized in a formulated product. The core may be a liquid at and around room temperature.

The core includes perfume. The core may comprise from about 1 wt % to 100 wt % perfume, based on the total weight of the core. Preferably, the core can include 50 wt % to 100 wt % perfume based on the total weight of the core, more preferably 80 wt % to 100 wt % perfume based on the total weight of the core. Typically, higher levels of perfume are preferred for improved delivery efficiency.

The perfume may comprise one or more, preferably two or more, perfume raw materials. The term "perfume raw material" (or "PRM") as used herein refers to compounds having a molecular weight of at least about 100 g/mol and which are useful in imparting an odor, fragrance, essence, or scent, either alone or with other perfume raw materials. Typical PRMs comprise inter alia alcohols, ketones, aldehydes, esters, ethers, nitriles and alkenes, such as terpene. A listing of common PRMs can be found in various reference sources, for example, "Perfume and Flavor Chemicals", Vols. I and II; Steffen Arctander Allured Pub. Co. (1994) and "Perfumes: Art, Science and Technology", Miller, P. M. and Lamparsky, D., Blackie Academic and Professional (1994).

The PRMs may be characterized by their boiling points (B.P.) measured at the normal pressure (760 mm Hg), and their octanol/water partitioning coefficient (P), which may be described in terms of log P, determined according to the test method below. Based on these characteristics, the PRMs may be categorized as Quadrant I, Quadrant II, Quadrant III, or Quadrant IV perfumes, as described in more detail below. A perfume having a variety of PRMs from different quadrants may be desirable, for example, to provide fragrance benefits at different touchpoints during normal usage.

Perfume raw materials having a boiling point B.P. lower than about 250° C. and a log P lower than about 3 are known as Quadrant I perfume raw materials. Quadrant 1 perfume raw materials are preferably limited to less than 30% of the perfume composition. Perfume raw materials having a B.P. of greater than about 250° C. and a log P of greater than about 3 are known as Quadrant IV perfume raw materials, perfume raw materials having a B.P. of greater than about 250° C. and a log P lower than about 3 are known as Quadrant II perfume raw materials, perfume raw materials having a B.P. lower than about 250° C. and a log P greater than about 3 are known as a Quadrant III perfume raw materials. Suitable Quadrant I, II, III and IV perfume raw materials are disclosed in U.S. Pat. No. 6,869,923 B1.

The perfume micro-capsule comprises a perfume. Preferably, the perfume of the microcapsule comprises a mixture of at least 3, or even at least 5, or at least 7 perfume raw materials. The perfume of the micro-capsule may comprise at least 10 or at least 15 perfume raw materials. A mixture of perfume raw materials may provide more complex and desirable aesthetics, and/or better perfume performance or longevity, for example at a variety of touchpoints. However, it may be desirable to limit the number of perfume raw materials in the perfume to reduce or limit formulation complexity and/or cost.

The perfume may comprise at least one perfume raw material that is naturally derived. Such components may be desirable for sustainability/environmental reasons. Naturally derived perfume raw materials may include natural extracts or essences, which may contain a mixture of PRMs. Such natural extracts or essences may include orange oil, lemon oil, rose extract, lavender, musk, patchouli, balsamic essence, sandalwood oil, pine oil, cedar, and the like.

The core may comprise, in addition to perfume raw materials, a pro-perfume, which can contribute to improved longevity of freshness benefits. Pro-perfumes may comprise nonvolatile materials that release or convert to a perfume material as a result of, e.g., simple hydrolysis, or may be pH-change-triggered pro-perfumes (e.g. triggered by a pH drop) or may be enzymatically releasable pro-perfumes, or light-triggered pro-perfumes. The pro-perfumes may exhibit varying release rates depending upon the pro-perfume chosen.

The core of the encapsulates of the present disclosure may comprise a core modifier, such as a partitioning modifier and/or a density modifier. The core may comprise, in addition to the perfume, from greater than 0% to 80%, preferably from greater than 0% to 50%, more preferably from greater than 0% to 30% based on total core weight, of a core modifier. The partitioning modifier may comprise a material selected from the group consisting of vegetable oil, modified vegetable oil, mono-, di-, and tri-esters of $C_4$-$C_{24}$ fatty acids, isopropyl myristate, dodecanophenone, lauryl laurate, methyl behenate, methyl laurate, methyl palmitate, methyl stearate, and mixtures thereof. The partitioning modifier may preferably comprise or consist of isopropyl myristate. The modified vegetable oil may be esterified and/or brominated. The modified vegetable oil may preferably comprise castor oil and/or soybean oil. US Patent Application Publication 20110268802, incorporated herein by reference, describes other partitioning modifiers that may be useful in the presently described perfume encapsulates.

ii. Shell

The capsules of the present disclosure include a shell that surrounds the core.

The shell can include a first shell component and optionally a second shell component that surrounds the first shell component. The first shell component can include a condensed layer formed from the condensation product of a precursor. As described in detail below, the precursor can include one or more precursor compounds. The first shell component can include a nanoparticle layer. The second shell component can include inorganic materials.

The shell may be substantially inorganic (defined later). The substantially inorganic shell can include a first shell component comprising a condensed layer surrounding the core and may further comprise a nanoparticle layer surrounding the condensed layer. The substantially inorganic shell may further comprise a second shell component surrounding the first shell component. The first shell component comprises inorganic materials, preferably metal/semi-metal oxides, more preferably SiO2, TiO2 and Al2O3, and even more preferably SiO2. The second shell component comprises inorganic material, preferably comprising materials from the groups of Metal/semi-metal oxides, metals and minerals, more preferably materials chosen from the list of $SiO_2$, $TiO_2$, $Al_2O_3$, $ZrO_2$, $ZnO_2$, $CaCO_3$, $Ca_2SiO_4$, $Fe_2O_3$, $Fe_3O_4$, clay, gold, silver, iron, nickel, and copper, even more preferably chosen from $SiO_2$ and $CaCO_3$. Preferably, the second shell component material is of the same type of chemistry as the first shell component in order to maximize chemical compatibility.

The first shell component can include a condensed layer surrounding the core. The condensed layer can be the condensation product of one or more precursors. The one or more precursors may comprise at least one compound from the group consisting of Formula (I), Formula (II), and a mixture thereof, wherein Formula (I) is $(M'O_zY_n)_w$, and wherein Formula (II) is $(M'O_zY_nR^1_p)_w$. It may be preferred that the precursor comprises only Formula (I) and is free of compounds according to Formula (II), for example so as to reduce the organic content of the capsule shell (i.e., no $R^1$ groups). Formulas (I) and (II) are described in more detail below.

The one or more precursors can be of Formula (I):

$$(M'O_zY_n)_w \qquad \text{(Formula I)},$$

where M is one or more of silicon, titanium and aluminum, v is the valence number of M and is 3 or 4, z is from 0.5 to 1.6, preferably 0.5 to 1.5, each Y is independently selected from —OH, —OR$^2$, —NH$_2$, —NHR$^2$, —N(R$^2$)$_2$, wherein $R^2$ is a $C_1$ to $C_{20}$ alkyl, $C_1$ to $C_{20}$ alkylene, $C_6$ to $C_{22}$ aryl, or a 5-12 membered heteroaryl comprising from 1 to 3 ring heteroatoms selected from O, N, and S, $R^3$ is a H, $C_1$ to $C_{20}$ alkyl, $C_1$ to $C_{20}$ alkylene, $C_6$ to $C_{22}$ aryl, or a 5-12 membered heteroaryl comprising from 1 to 3 ring heteroatoms selected from O, N, and S, n is from 0.7 to (v−1), and w is from 2 to 2000.

The one or more precursors can be of Formula (I) where M is silicon. It may be that Y is —OR$^2$. It may be that n is 1 to 3. It may be preferable that Y is —OR$^2$ and n is 1 to 3. It may be that n is at least 2, one or more of Y is —OR$^2$, and one or more of Y is –OH.

$R^2$ may be $C_1$ to $C_{20}$ alkyl. $R^2$ may be $C_6$ to $C_{22}$ aryl. $R^2$ may be one or more of $C_1$ alkyl, $C_2$ alkyl, $C_3$ alkyl, $C_4$ alkyl, $C_5$ alkyl, $C_6$ alkyl, $C_7$ alkyl, and $C_8$ alkyl. $R^2$ may be $C_1$ alkyl. $R^2$ may be $C_2$ alkyl. $R^2$ may be $C_3$ alkyl. $R^2$ may be $C_4$ alkyl.

It may be that z is from 0.5 to 1.3, or from 0.5 to 1.1, 0.5 to 0.9, or from 0.7 to 1.5, or from 0.9 to 1.3, or from 0.7 to 1.3.

It may be preferred that M is silicon, v is 4, each Y is —OR$^2$, n is 2 and/or 3, and each R$^2$ is $C_2$ alkyl.

The precursor can include polyalkoxysilane (PAOS). The precursor can include polyalkoxysilane (PAOS) synthesized via a hydrolytic process.

The precursor can alternatively or further include one or more of a compound of Formula (II):

$$(M'O_zY_nR^1_p)_w \qquad \text{(Formula II)},$$

where M is one or more of silicon, titanium and aluminum, v is the valence number of M and is 3 or 4, z is from 0.5 to 1.6, preferably 0.5 to 1.5, each Y is independently selected from —OH, —OR$^2$, —NH$_2$, —NHR$^2$, —N(R$^2$)$_2$, wherein $R^2$ is selected from a $C_1$ to $C_{20}$ alkyl, $C_1$ to $C_{20}$ alkylene, $C_6$ to $C_{22}$ aryl, or a 5-12 membered heteroaryl comprising from 1 to 3 ring heteroatoms selected from O, N, and S, $R^3$ is a H, $C_1$ to $C_{20}$ alkyl, $C_1$ to $C_{20}$ alkylene, $C_6$ to $C_{22}$ aryl, or a 5-12 membered heteroaryl comprising from 1 to 3 ring heteroatoms selected from O, N, and S, n is from 0 to (v−1), each $R^1$ is independently selected from a $C_1$ to $C_{30}$ alkyl, a $C_1$ to $C_{30}$ alkylene, a $C_1$ to $C_{30}$ alkyl substituted with one or more of a halogen, —OCF$_3$, —NO$_2$, —CN, —NC, —OH, —OCN, —NCO, alkoxy, epoxy, amino, mercapto, acryloyl, CO$_2$H, CO$_2$alkyl, aryl, and heteroaryl, or a $C_1$ to $C_{30}$ alkylene substituted with one or more of a halogen, —OCF$_3$, —NO$_2$, —CN, —NC, —OH, —OCN, —NCO, alkoxy, epoxy, amino, mercapto, acryloyl, CO$_2$H, CO$_2$alkyl, aryl, and heteroaryl, p is present in an amount up to pmax, and w is from 2 to 2000; wherein pmax=60/[9*Mw(R$^1$)+8], where Mw(R$^1$) is the molecular weight of the R$^1$ group.

$R^1$ may be a $C_1$ to $C_{30}$ alkyl substituted with one to four groups independently selected from a halogen, —OCF$_3$, —NO$_2$, —CN, —NC, —OH, —OCN, —NCO, alkoxy, epoxy, amino, mercapto, acryloyl, CO$_2$H, CO$_2$alkyl, aryl, and heteroaryl. $R^1$ may be a $C_1$ to $C_{30}$ alkylene substituted with one to four groups independently selected from a halogen, —OCF$_3$, —NO$_2$, —CN, —NC, —OH, —OCN, —NCO, alkoxy, epoxy, amino, mercapto, acryloyl, CO$_2$H, CO$_2$alkyl, aryl, and heteroaryl.

As indicated above, to reduce or even eliminate organic content in the first shell component, it may be preferred to reduce, or even eliminate, the presence of compounds according to Formula (II), which has R1 groups. The precursor, the condensed layer, the first shell component, and/or the shell may be free of compounds according to Formula (II).

The precursors of Formula (I) and/or (II) may be characterized by one or more physical properties, namely a molecular weight (Mw), a degree of branching (DB) and a polydispersity index (PDI) of the molecular weight distribution. It is believed that selecting particular Mw and/or DB can be useful to obtain capsules that hold their mechanical integrity once left drying on a surface and that have low shell permeability in surfactant-based matrices. The precursors of Formula (I) and (II) may be characterized as having a DB between 0 and 0.6, preferably between 0.1 and 0.5, more preferably between 0.19 and 0.4, and/or a Mw between 600 Da and 100000 Da, preferably between 700 Da and 60000 Da, more preferably between 1000 Da and 30000 Da. The characteristics provide useful properties of said precursor in order to obtain capsules of the present invention. The precursors of Formula (I) and/or (II) can have a PDI between 1 and 50.

The condensed layer comprising metal/semi-metal oxides may be formed from the condensation product of a precursor comprising at least one compound of Formula (I) and/or at least one compound of Formula (II), optionally in combination with one or more monomeric precursors of metal/semi-metal oxides, wherein said metal/semi-metal oxides comprise TiO2, Al2O3 and SiO2, preferably SiO2. The monomeric precursors of metal/semi-metal oxides may include compounds of the formula $M(Y)_{v-n}R_n$ wherein M, Y and R are defined as in Formula (II), and n can be an integer between 0 and 3. The monomeric precursor of metal/semi-metal oxides may be preferably of the form where M is Silicon wherein the compound has the general formula $Si(Y)_{4-n}R_n$ wherein Y and R are defined as for Formula (II). Examples of such monomers are TEOS (tetraethoxy orthosilicate), TMOS (tetramethoxy orthosilicate), TBOS (tetrabutoxy orthosilicate), triethoxymethylsilane (TEMS), diethoxy-dimethylsilane (DEDMS), trimethylethoxysilane (TMES), and tetraacetoxysilane (TAcS). These are not meant to be limiting the scope of monomers that can be used and it would be apparent to the person skilled in the art what are the suitable monomers that can be used in combination herein.

The first shell components can include an optional nanoparticle layer. The nanoparticle layer comprises nanoparticles. The nanoparticles of the nanoparticle layer can be one or more of SiO$_2$, TiO$_2$, Al$_2$O$_3$, ZrO$_2$, ZnO$_2$, CaCO$_3$, clay, silver, gold, and copper. Preferably, the nanoparticle layer can include SiO$_2$ nanoparticles.

The nanoparticles can have an average diameter between 1 nm and 500 nm, preferably between 50 nm and 400 nm.

The pore size of the capsules can be adjusted by varying the shape of the nanoparticles and/or by using a combination of different nanoparticle sizes. For example, non-spherical irregular nanoparticles can be used as they can have improved packing in forming the nanoparticle layer, which is believed to yield denser shell structures. This can be advantageous when limited permeability is required. The nanoparticles used can have more regular shapes, such as spherical. Any contemplated nanoparticle shape can be used herein.

The nanoparticles can be substantially free of hydrophobic modifications. The nanoparticles can be substantially free of organic compound modifications. The nanoparticles can include an organic compound modification. The nanoparticles can be hydrophilic.

The nanoparticles can include a surface modification such as but not limited to linear or branched $C_1$ to $C_{20}$ alkyl groups, surface amino groups, surface methacrylo groups, surface halogens, or surface thiols. These surface modifications are such that the nanoparticle surface can have covalently bound organic molecules on it. When it is disclosed in this document that inorganic nanoparticles are used, this is meant to include any or none of the aforementioned surface modifications without being explicitly called out.

The capsules of the present disclosure may be defined as comprising a substantially inorganic shell comprising a first shell component and a second shell component. By substantially inorganic it is meant that the first shell component can comprise up to 10 wt %, or up to 5 wt % of organic content, preferably up to 1 wt % of organic content, as defined later in the organic content calculation. It may be preferred that the first shell component, the second shell component, or both comprises no more than about 5 wt %, preferably no more than about 2 wt %, more preferably about 0 wt %, of organic content, by weight of the first or shell component, as the case may be.

While the first shell component is useful to build a mechanically robust scaffold or skeleton, it can also provide low shell permeability in liquid products containing surfactants such as laundry detergents, shower-gels, cleansers, etc. (see Surfactants in Consumer Products, J. Falbe, Springer-Verlag). The second shell component can greatly reduce the shell permeability, which improves the capsule impermeability in surfactant-based matrices. A second shell component can also greatly improve capsule mechanical properties, such as a capsule rupture force and fracture strength. Without intending to be bound by theory, it is believed that a second shell component contributes to the densification of the overall shell by depositing a precursor in pores remaining in the first shell component. A second shell component also adds an extra inorganic layer onto the surface of the capsule. These improved shell permeabilities and mechanical properties provided by the $2^{nd}$ shell component only occur when used in combination with the first shell component as defined in this invention.

More detailed descriptions of the shell structure, their materials and how these interact with each other to provide optimal performance can be found in U.S. patent application Ser. Nos. 16/851,173, 16/851,176, and 16/851,194, whose disclosures in their entirety are incorporated herein by reference.

iii. Process of Making Capsules

Capsules of the present disclosure may be formed by first admixing a hydrophobic material with any of the precursors of the condensed layer as defined above, thus forming the oil phase, wherein the oil phase can include an oil-based and/or oil-soluble precursor. Said precursor/hydrophobic material mixture is then either used as a dispersed phase or as a continuous phase in conjunction with a water phase, where in the former case an O/W (oil-in-water) emulsion is formed and in the latter a W/O (water-in-oil) emulsion is formed once the two phases are mixed and homogenized via methods that are known to the person skilled in the art. Nanoparticles can be present in the water phase and/or the oil phase, irrespective of the type of emulsion that is desired. The oil phase can include an oil-based core modifier and/or an oil-based benefit agent and a precursor of the condensed layer. Suitable core materials to be used in the oil phase are described earlier in this document.

Once either emulsion is formed, the following steps may occur:

(a) the nanoparticles migrate to the oil/water interface, thus forming the nanoparticle layer.

(b) The precursor of the condensed layer comprising precursors of metal/semi-metal oxides will start undergoing a hydrolysis/condensation reaction with the water at the oil/water interface, thus forming the condensed layer surrounded by the nanoparticle layer. The precursors of the condensed layer can further react with the nanoparticles of the nanoparticle layer.

The precursor forming the condensed layer can be present in an amount between 1 wt % and 50 wt %, preferably between 10 wt % and 40 wt % based on the total weight of the oil phase.

The oil phase composition can include any compounds as defined in the core section above. The oil phase, prior to emulsification, can include between 10 wt % to about 99 wt % benefit agent.

In the method of making capsules according to the present disclosure, the oil phase may be the dispersed phase, and the continuous aqueous (or water) phase can include water, an acid or base, and nanoparticles. The aqueous (or water) phase may have a pH between 1 and 11, preferably between 1 and 7 at least at the time of admixing both the oil phase and the aqueous phase together. The acid can be a strong acid. The strong acid can include one or more of HCl, $HNO_3$, $H_2SO_4$, HBr, HI, $HClO_4$, and $HClO_3$, preferably HCl. The acid can be a weak acid. The weak acid can be acetic acid or HF. The concentration of the acid in the continuous aqueous phase can be between $10^{-7}$M and 5M. The base can be a mineral or organic base, preferably a mineral base. The mineral base can be a hydroxide, such as sodium hydroxide and ammonia. For example, the mineral base can be about $10^{-5}$ M to 0.01M NaOH, or about $10^{-5}$ M to about 1M ammonia. The list of acids and bases and their concentration ranges exemplified above is not meant to be limiting the scope of the invention, and other suitable acids and bases that allow for the control of the pH of the continuous phase are contemplated herein.

In the method of making the capsules according to the present disclosure, the pH can be varied throughout the process by the addition of an acid and/or a base. For example, the method can be initiated with an aqueous phase at an acidic or neutral pH and then a base can be added during the process to increase the pH. Alternatively, the method can be initiated with an aqueous phase at a basic or neutral pH and then an acid can be added during the process to decrease the pH. Still further, the method can be initiated with an aqueous phase at an acid or neutral pH and an acid can be added during the process to further reduce the pH. Yet further the method can be initiated with an aqueous phase at a basic or neutral pH and a base can be added during the process to further increase the pH. Any suitable pH shifts can be used. Further any suitable combinations of acids and bases can be used at any time in the method to achieve a desired pH. Any of the nanoparticles described above can be used in the aqueous phase. The nanoparticles can be present in an amount of about 0.01 wt % to about 10 wt % based on the total weight of the aqueous phase.

The method can include admixing the oil phase and the aqueous phase in a ratio of oil phase to aqueous phase of about 1:10 to about 1:1.

The second shell component can be formed by admixing capsules having the first shell component with a solution of second shell component precursor. The solution of second shell component precursor can include a water soluble or oil soluble second shell component precursor. The second shell component precursor can be one or more of a compound of Formula (I) as defined above, tetraethoxysilane (TEOS), tetramethoxysilane (TMOS), tetrabutoxysilane (TBOS), triethoxymethylsilane (TEMS), diethoxy-dimethylsilane (DEDMS), trimethylethoxysilane (TMES), and tetraacetoxysilane (TAcS). The second shell component precursor can also include one or more of silane monomers of type $Si(YR)_{4-n}R_n$, wherein YR is a hydrolysable group and R is a non-hydrolysable group. Examples of such monomers are given earlier in this paragraph, and these are not meant to be limiting the scope of monomers that can be used. The second shell component precursor can include salts of silicate, titanate, aluminate, zirconate and/or zincate. The second shell component precursor can include carbonate and calcium salts. The second shell component precursor can include salts of iron, silver, copper, nickel, and/or gold. The second shell component precursor can include zinc, zirconium, silicon, titanium, and/or aluminum alkoxides. The second shell component precursor can include one or more of silicate salt solutions such as sodium silicates, silicon tetralkoxide solutions, iron sulfate salt and iron nitrate salt, titanium alkoxides solutions, aluminum trialkoxide solutions, zinc dialkoxide solutions, zirconium alkoxide solutions, calcium salt solution, carbonate salt solution. A second shell component comprising $CaCO_3$ can be obtained from a combined use of calcium salts and carbonate salts. A second shell component comprising $CaCO_3$ can be obtained from Calcium salts without addition of carbonate salts, via in-situ generation of carbonate ions from $CO_2$.

The second shell component precursor can include any suitable combination of any of the foregoing listed compounds.

The solution of second shell component precursor can be added dropwise to the capsules comprising a first shell component. The solution of second shell component precursor and the capsules can be mixed together between 1 minute and 24 hours. The solution of second shell component precursor and the capsules can be mixed together at room temperature or at elevated temperatures, such as 20° C. to 100° C.

The second shell component precursor solution can include the second shell component precursor in an amount between 1 wt % and 50 wt % based on the total weight of the solution of second shell component precursor.

Capsules with a first shell component can be admixed with the solution of the second shell component precursor at a pH of between 1 and 11. The solution of the second shell precursor can contain an acid and/or a base. The acid can be a strong acid. The strong acid can include one or more of HCl, $HNO_3$, $H_2SO_4$, HBr, HI, $HClO_4$, and $HClO_3$, preferably HCl. In other embodiments, the acid can be a weak acid. In embodiments, said weak acid can be acetic acid or HF. The concentration of the acid in the second shell component precursor solution can be between $10^{-7}$M and 5M. The base can be a mineral or organic base, preferably a mineral base. The mineral base can be a hydroxide, such as sodium hydroxide and ammonia. For example, the mineral base can be about $10^{-5}$ M to 0.01M NaOH, or about $10^{-5}$ M to about 1M ammonia. The list of acids and bases exemplified above is not meant to be limiting the scope of the invention, and other suitable acids and bases that allow for the control of the pH of the second shell component precursor solution are contemplated herein.

The process of forming a second shell component can include a change in pH during the process. For example, the process of forming a second shell component can be initiated at an acidic or neutral pH and then a base can be added during the process to increase the pH. Alternatively, the process of forming a second shell component can be initiated at a basic or neutral pH and then an acid can be added during the process to decrease the pH. Still further, the process of forming a second shell component can be initiated at an acid or neutral pH and an acid can be added during the process to further reduce the pH. Yet further the process of forming a second shell component can be initiated at a basic or neutral pH and a base can be added during the process to further increase the pH. Any suitable pH shifts can be used. Further any suitable combinations of acids and bases can be used at any time in the solution of second shell component precursor to achieve a desired pH. The process of forming a second shell component can include maintaining a stable pH during the process with a maximum deviation of +/−0.5 pH unit. For example, the process of forming a second shell component can be maintained at a basic, acidic or neutral pH. Alternatively, the process of forming a second shell component can be maintained at a specific pH range by controlling the pH using an acid or a base. Any suitable pH range can be used. Further any suitable combinations of acids and bases can be used at any time in the solution of second shell component precursor to keep a stable pH at a desirable range.

More detailed descriptions of the method of making the capsules and the relevant properties of all shell component precursors (i.e. condensed layer precursors, nanoparticles and second shell component precursors) can be found in U.S. patent application Ser. Nos. 16/851,173, 16/851,176, and 16/851,194, whose disclosures in their entirety are defining the method of making of the capsules of the present invention.

Whether making an oil-based core or aqueous core, the emulsion can be cured under conditions to solidify the precursor thereby forming the shell surrounding the core.

The reaction temperature for curing can be increased in order to increase the rate at which solidified capsules are obtained. The curing process can induce condensation of the precursor. The curing process can be done at room temperature or above room temperature. The curing process can be done at temperatures 30° C. to 150° C., preferably 50° C. to 120° C., more preferably 80° C. to 100° C. The curing process can be done over any suitable period to enable the capsule shell to be strengthened via condensation of the precursor material. The curing process can be done over a period from 1 minute to 45 days, preferably 1 hour to 7 days, more preferably 1 hour to 24 hours. Capsules are considered cured when they no longer collapse. Determination of capsule collapse is detailed below. During the curing step, it is believed that hydrolysis of Y moieties (from Formula (I) and/or (II)) occurs, followed by the subsequent condensation of a —OH group with either another —OH group or another moiety of type Y (where the 2 Y moieties are not necessarily the same). The hydrolysed precursor moieties will initially condense with the surface moieties of the nanoparticles (provided they contain such moieties). As the shell formation progresses, the precursor moieties will react with said preformed shell.

To test whether capsules collapse, the slurry must be diluted (by at least 10 times) into de-ionized water. Drops of the subsequent dilution are added onto a microscopy microslide and left to dry overnight at room temperature. The following day the dried capsules are observed under an optical microscope (without the use of a cover slide) by light transmission to assess if the capsules have retained their spherical shape.

The emulsion can be cured such that the shell precursor undergoes condensation. The emulsion can be cured such that the shell precursor reacts with the nanoparticles to undergo condensation. Shown below are examples of the hydrolysis and condensation steps described herein for silica-based shells:

Hydrolysis: ≡Si—OR+H$_2$O→≡Si—OH+ROH

Condensation: ≡Si—OH+≡Si—OR→≡Si—O—Si≡+ROH

≡Si—OH+≡Si—OH→≡Si—O—Si≡+H$_2$O.

For example, when a precursor of Formula (I) or (II) is used, the following describes the hydrolysis and condensation steps:

Hydrolysis: ≡M-Y+H$_2$O→≡M-OH+YH

Condensation: ≡M-OH+≡M-Y→≡M-O-M≡+YH

≡M-OH+≡M-OH→≡M-O-M≡+H$_2$O.

The capsules may be provided as a slurry composition (or simply "slurry" herein). The result of the methods described herein may be a slurry containing the capsules. The slurry can be formulated into a product, such as a consumer product.

Additional Perfume Delivery Systems

In addition to the capsules of the present disclosure, the composition may comprise one or more additional perfume delivery systems. The additional perfume delivery system may comprise free perfume, pro-perfumes, other perfume capsules (for example core-shell capsules that include greater than 5 wt % of organic material in the shell), and mixtures thereof.

To fight malodors, it may be particularly effective that the perfume delivery system comprises free (e.g., unencapsulated) perfume. The composition may comprise from 0.01% to 10%, or from 0.1% to 5%, or even from 0.2% to 2% by weight of free perfume. The composition may comprise at least 0.75% or at least 1%, by weight of the composition, of free perfume. Preferably, the free perfume comprises a mixture of at least 3, or even at least 5, or at least 7, or at least 10, or at least 15 perfume raw materials.

The compositions of the present disclosure may comprise a pro-perfume, which can contribute to improved longevity of freshness benefits. Pro-perfumes may comprise nonvolatile materials that release or convert to a perfume material as a result of, e.g., simple hydrolysis, or may be pH-change-triggered pro-perfumes (e.g. triggered by a pH drop) or may be enzymatically releasable pro-perfumes, or light-triggered pro-perfumes. The pro-perfumes may exhibit varying release rates depending upon the pro-perfume chosen.

The composition may comprise other perfume capsules. These capsules may be core-shell capsules and may include more than 5 wt % organic material in the shell, by weight of the shell material. Such capsules may be considered "organic" capsules in the present disclosure in order to differentiate them from the inorganic capsules described and claimed herein. The shell material of the organic capsules may comprise a material, preferably a polymeric material, derived from melamine, polyacrylamide, silicones, polystyrene, polyurea, polyurethanes, polyacrylate based materials, gelatin, styrene malic anhydride, polyamides, and mixtures thereof. The organic capsules may be coated with a deposition aid, a cationic polymer, a non-ionic polymer, an anionic polymer, or mixtures thereof. Suitable deposition polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, cationic polysaccharides (such as chitosan), and combinations thereof. The organic capsules may have a volume-weighted mean particle size from about 0.5 microns to about 100 microns, preferably from about 1 microns to about 60 microns, or alternatively a volume weighted mean particle size from about, from about 25 microns to about 60 microns, more preferably from about 25 microns to about 60 microns.

Process of Making

The present disclosure relates to processes for making any of the antiperspirant and/or deodorant compositions described herein. The process of making an antiperspirant or deodorant composition may comprise the step of combining a capsule as described herein with a liquid carrier in the antiperspirant or deodorant composition. For deodorant compositions that comprise an emulsion, the capsule may be added before or after the emulsion is formed. For deodorant compositions that comprise a structurant, the capsule may be added before or after the structurant is added.

The antiperspirant and deodorant compositions of the present disclosure can be formulated into any suitable form and prepared by any process chosen by the formulator. The antiperspirant and deodorant actives, the capsules, and other adjuncts, if any, may be combined in a batch process, in a circulation loop process, and/or by an in-line mixing process. Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders.

Method of Using

The antiperspirant and deodorant compositions of the present invention may be topically applied to the axilla or other area of the skin in any known or otherwise effective method for controlling malodor associated with perspiration. These methods comprise applying to the axilla or other area of the human skin an effective amount of the deodorant composition of the present invention, typically about 0.1 gram per axilla to about 2.0 gram per axilla.

TEST METHODS

It is understood that the test methods that are disclosed in the Test Methods Section of the present application should be used to determine the respective values of the parameters of Applicant's claimed subject matter as claimed and described herein.

Method to Determine Log P

The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Viscosity Method

The viscosity of neat product is determined using a Brookfield® DV-E rotational viscometer, spindle 2, at 60 rpm, at about 20-21° C.

Mean Shell Thickness Measurement

The capsule shell, including the first shell component and the second shell component, when present, is measured in nanometers on twenty benefit agent containing delivery capsules making use of a Focused Ion Beam Scanning Electron Microscope (FIB-SEM; FEI Helios Nanolab 650) or equivalent. Samples are prepared by diluting a small volume of the liquid capsule dispersion (20 µl) with distilled water (1:10). The suspension is then deposited on an ethanol cleaned aluminium stub and transferred to a carbon coater (Leica EM ACE600 or equivalent). Samples are left to dry under vacuum in the coater (vacuum level: $10^{-5}$ mbar). Next 25-50 nm of carbon is flash deposited onto the sample to deposit a conductive carbon layer onto the surface. The aluminium stubs are then transferred to the FIB-SEM to prepare cross-sections of the capsules. Cross-sections are prepared by ion milling with 2.5 nA emission current at 30 kV accelerating voltage using the cross-section cleaning pattern. Images are acquired at 5.0 kV and 100 pA in immersion mode (dwell time approx. 10 µs) with a magnification of approx. 10,000.

Images are acquired of the fractured shell in cross-sectional view from 20 benefit delivery capsules selected in a random manner which is unbiased by their size, to create a representative sample of the distribution of capsules sizes present. The shell thickness of each of the 20 capsules is measured using the calibrated microscope software at 3 different random locations, by drawing a measurement line perpendicular to the tangent of the outer surface of the capsule shell. The 60 independent thickness measurements are recorded and used to calculate the mean thickness.

Mean and Coefficient of Variation of Volume-Weighted Capsule Diameter

Capsule size distribution is determined via single-particle optical sensing (SPOS), also called optical particle counting (OPC), using the AccuSizer 780 AD instrument or equivalent and the accompanying software CW788 version 1.82 (Particle Sizing Systems, Santa Barbara, California, U.S.A.), or equivalent. The instrument is configured with the following conditions and selections: Flow Rate=1 mL/sec; Lower Size Threshold=0.50 µm; Sensor Model Number=LE400-05SE or equivalent; Auto-dilution=On; Collection time=60 sec; Number channels=512; Vessel fluid volume=50 ml; Max coincidence=9200. The measurement is initiated by putting the sensor into a cold state by flushing with water until background counts are less than 100. A sample of delivery capsules in suspension is introduced, and its density of capsules adjusted with DI water as necessary via autodilution to result in capsule counts of at most 9200 per mL. During a time period of 60 seconds the suspension is analyzed. The range of size used was from 1 µm to 493.3 µm.

Volume Distribution:

$$CoVv(\%) = \frac{\sigma_v}{\mu_v} * 100$$

$$\sigma v = \sum_{i=1\ um}^{493.3\ um} (x_{i,v} * (d_i - \mu_v)^2) 0.5$$

$$\mu_v = \frac{\sum_{i=1\ um}^{493.3\ um} (x_{i,v} * d_i)}{\sum_{i=1\ um}^{493.3\ um} x_{i,v}}$$

where:

$CoV_v$—Coefficient of variation of the volume weighted size distribution $\sigma_v$—Standard deviation of volume-weighted size distribution $\mu_v$—mean of volume-weighted size distribution $d_i$—diameter in fraction i $x_{i,v}$—frequency in fraction i (corresponding to diameter i) of volume-weighted size distribution $$x_{i,v} = \frac{x_{i,n} * d_i^3}{\sum_{i=1\ um}^{493.3\ um} (x_{i,n} * d_i^3)}$$

Effective Volumetric Core-Shell Ratio Evaluation

The effective volumetric core-shell ratio values were determined as follows, which relies upon the mean shell thickness as measured by the Shell Thickness Test Method. The effective volumetric core-shell ratio of capsules where their mean shell thickness was measured is calculated by the following equation:

$$\frac{Core}{Shell} = \frac{\left(1 - \frac{2*Thickness}{D_{caps}}\right)^3}{\left(1 - \left(1 - \frac{2*Thickness}{D_{caps}}\right)^3\right)}$$

wherein Thickness is the mean shell thickness of a population of capsules measured by FIBSEM and the $D_{caps}$ is the mean volume weighted diameter of the population of capsules measured by optical particle counting.

This ratio can be translated to fractional core-shell ratio values by calculating the core weight percentage using the following equation:

$$\% \ Core = \left(\frac{\frac{Core}{Shell}}{1 + \frac{Core}{Shell}}\right) * 100$$

and shell percentage can be calculated based on the following equation:

% Shell=100−% Core.

Degree of Branching Method

The degree of branching of the precursors was determined as follows: Degree of branching is measured using (29Si) Nuclear Magnetic Resonance Spectroscopy (NMR).

Sample Preparation

Each sample is diluted to a 25% solution using deuterated benzene (Benzene-D6 "100%" (D, 99.96% available from Cambridge Isotope Laboratories Inc., Tewksbury, MA, or equivalent). 0.015M Chromium(III) acetylacetonate (99.99% purity, available from Sigma-Aldrich, St. Louis, MO, or equivalent) is added as a paramagnetic relaxation reagent. If glass NMR tubes (Wilmed-LabGlass, Vineland, NJ or equivalent) are used for analysis, a blank sample must also be prepared by filling an NMR tube with the same type of deuterated solvent used to dissolve the samples. The same glass tube must be used to analyze the blank and the sample.

Sample Analysis

The degree of branching is determined using a Bruker 400 MHz Nuclear Magnetic Resonance Spectroscopy (NMR) instrument, or equivalent. A standard silicon (29Si) method (e.g. from Bruker) is used with default parameter settings with a minimum of 1000 scans and a relaxation time of 30 seconds.

Sample Processing

The samples are stored and processed using system software appropriate for NMR spectroscopy such as MestReNova version 12.0.4-22023 (available from Mestrelab Research) or equivalent. Phase adjusting and background correction are applied. There is a large, broad, signal present that stretches from −70 to −136 ppm which is the result of using glass NMR tubes as well as glass present in the probe housing. This signal is suppressed by subtracting the spectra of the blank sample from the spectra of the synthesized sample provided that the same tube and the same method parameters are used to analyze the blank and the sample. To further account for any slight differences in data collection, tubes, etc., an area outside of the peaks of interest area should be integrated and normalized to a consistent value. For example, integrate −117 to −115 ppm and set the integration value to 4 for all blanks and samples.

The resulting spectra produces a maximum of five main peak areas. The first peak (Q0) corresponds to unreacted TAOS. The second set of peaks (Q1) corresponds to end groups. The next set of peaks (Q2) correspond to linear groups. The next set of broad peaks (Q3) are semi-dendritic units. The last set of broad peaks (Q4) are dendritic units. When PAOS and PBOS are analyzed, each group falls within a defined ppm range. Representative ranges are described in the following table:

| Group ID | # of Bridging Oxygen per Silicon | ppm Range |
|---|---|---|
| Q0 | 0 | −80 to −84 |
| Q1 | 1 | −88 to −91 |
| Q2 | 2 | −93 to −98 |
| Q3 | 3 | −100 to −106 |
| Q4 | 4 | −108 to −115 |

Polymethoxysilane has a different chemical shift for Q0 and Q1, an overlapping signal for Q2, and an unchanged Q3 and Q4 as noted in the table below:

| Group ID | # of Bridging Oxygen per Silicon | ppm Range |
|---|---|---|
| Q0 | 0 | −78 to −80 |
| Q1 | 1 | −85 to −88 |
| Q2 | 2 | −91 to −96 |
| Q3 | 3 | −100 to −106 |
| Q4 | 4 | −108 to −115 |

The ppm ranges indicated in the tables above may not apply to all monomers. Other monomers may cause altered chemical shifts, however, proper assignment of Q0-Q4 should not be affected.

Using MestReNova, each group of peaks is integrated, and the degree of branching can be calculated by the following equation:

$$\text{Degree of Branching} = (1/4) * \frac{3*Q3 + 4*Q4}{Q1 + Q2 + Q3 + Q4}$$

Molecular Weight and Polydispersity Index Determination Method

The molecular weight (Polystyrene equivalent Weight Average Molecular Weight (Mw)) and polydispersity index (Mw/Mn) of the condensed layer precursors described herein are determined using Size Exclusion Chromatography with Refractive Index detection. Mn is the number average molecular weight.

Sample Preparation

Samples are weighed and then diluted with the solvent used in the instrument system to a targeted concentration of 10 mg/mL. For example, weigh 50 mg of polyalkoxysilane into a 5 mL volumetric flask, dissolve and dilute to volume with toluene. After the sample has dissolved in the solvent, it is passed through a 0.45 um nylon filter and loaded into the instrument autosampler.

Sample Analysis

An HPLC system with autosampler (e.g. Waters 2695 HPLC Separation Module, Waters Corporation, Milford MA, or equivalent) connected to a refractive index detector (e.g. Wyatt 2414 refractive index detector, Santa Barbara, CA, or equivalent) is used for polymer analysis. Separation is performed on three columns, each 7.8 mm I.D.×300 mm in length, packed with 5 µm polystyrene-divinylbenzene media, connected in series, which have molecular weight cutoffs of 1, 10, and 60 kDA, respectively. Suitable columns are the TSKGel G1000HHR, G2000HHR, and G3000HHR columns (available from TOSOH Bioscience, King of Prussia, PA) or equivalent. A 6 mm I.D.×40 mm long 5 µm polystyrene-divinylbenzene guard column (e.g. TSKgel Guardcolumn HHR-L, TOSOH Bioscience, or equivalent) is used to protect the analytical columns. Toluene (HPLC grade or equivalent) is pumped isocratically at 1.0 mL/min, with both the column and detector maintained at 25° C. 100 µL of the prepared sample is injected for analysis. The sample data is stored and processed using software with GPC calculation capability (e.g. ASTRA Version 6.1.7.17 software, available from Wyatt Technologies, Santa Barbara, CA or equivalent.)

The system is calibrated using ten or more narrowly dispersed polystyrene standards (e.g. Standard ReadyCal Set, (e.g. Sigma Aldrich, PN 76552, or equivalent) that have known molecular weights, ranging from about 0.250-70 kDa and using a third order fit for the Mp verses Retention Time Curve.

Using the system software, calculate and report Weight Average Molecular Weight (Mw) and PolyDispersity Index (Mw/Mn).

Method of Calculating Organic Content in First Shell Component

As used herein, the definition of organic moiety in the inorganic shell of the capsules according to the present disclosure is: any moiety X that cannot be cleaved from a metal precursor bearing a metal M (where M belongs to the group of metals and semi-metals, and X belongs to the group of non-metals) via hydrolysis of the M-X bond linking said moiety to the inorganic precursor of metal or semi-metal M and under specific reaction conditions, will be considered as organic. A minimal degree of hydrolysis of 1% when exposed to neutral pH distilled water for a duration of 24 h without stirring, is set as the reaction conditions.

This method allows one to calculate a theoretical organic content assuming full conversion of all hydrolysable groups. As such, it allows one to assess a theoretical percentage of organic for any mixture of silanes and the result is only indicative of this precursor mixture itself, not the actual organic content in the first shell component. Therefore, when a certain percentage of organic content for the first shell component is disclosed anywhere in this document, it is to be understood as containing any mixture of unhydrolyzed or pre-polymerized precursors that according to the below calculations give a theoretical organic content below the disclosed number.

Example for Silane (but not Limited Thereto; See Generic Formula at the End of this Section):

Consider a mixture of silanes, with a molar fraction $Y_i$ for each, and where i is an ID number for each silane. Said mixture can be represented as follows:

$$Si(XR)_{4-n_i}R_{n_i}$$

where XR is a hydrolysable group under conditions mentioned in the definition above, $R^i_{n_i}$ is non-hydrolysable under conditions mentioned above and $n_i$=0, 1, 2 or 3.

Such a mixture of silanes will lead to a shell with the following general formula:

$$SiO_{\frac{(4-n)}{2}}R_n$$

Then, the weight percentage of organic moieties as defined earlier can be calculated as follows:

1) Find out Molar fraction of each precursor (nanoparticles included)
2) Determine general formula for each precursor (nanoparticles included)
3) Calculate general formula of precursor and nanoparticle mixture based on molar fractions
4) Transform into reacted silane (all hydrolysable groups to oxygen groups)
5) Calculate weight ratio of organic moieties vs. total mass (assuming 1 mole of Si for framework)

EXAMPLE

| Raw material | Formula | Mw (g/mol) | weight (g) | amount (mmol) | Molar fraction |
|---|---|---|---|---|---|
| Sample AY | SiO(OEt)$_2$ | 134 | 1 | 7.46 | 0.57 |
| TEOS | Si(OEt)$_4$ | 208 | 0.2 | 0.96 | 0.07 |
| DEDMS | Si(OEt)$_2$Me$_2$ | 148.27 | 0.2 | 1.35 | 0.10 |
| SiO2 NP | SiO$_2$ | 60 | 0.2 | 3.33 | 0.25 |

To calculate the general formula for the mixture, each atoms index in the individual formulas is to be multiplied by their respective molar fractions. Then, for the mixture, a sum of the fractionated indexes is to be taken when similar ones occur (typically for ethoxy groups).

Note: Sum of all Si fractions will always add to 1 in the mixture general formula, by virtue of the calculation method (sum of all molar fractions for Si yields 1).

$$SiO_{1*0.57+2*0.25}(OEt)_{2*0.57+4*0.07+2*0.10}Me_{2*0.10}$$

$$SiO_{1.07}(OEt)_{1.62}Me_{0.20}$$

To transform the unreacted formula to a reacted one, simply divide the index of ALL hydrolysable groups by 2, and then add them together (with any pre-existing oxygen groups if applicable) to obtain the fully reacted silane.

$$SiO_{1.88}Me_{0.20}$$

In this case, the expected result is $SiO_{1.9}Me_{0.2}$, as the sum of all indexes must follow the following formula:

$$A+B/2=2,$$

where A is the oxygen atom index and B is the sum of all non-hydrolysable indexes. The small error occurs from rounding up during calculations and should be corrected. The index on the oxygen atom is then readjusted to satisfy this formula.

Therefore, the final formula is $SiO_{1.9}Me_{0.2}$, and the weight ratio of organic is calculated below:

Weight ratio=(0.20*15)/(28+1.9*16+0.20*15)=4.9%

General Case:

The above formulas can be generalized by considering the valency of the metal or semi-metal M, thus giving the following modified formulas:

$$M(XR)_{V-n_i}R^i_{n_i}$$

and using a similar method but considering the valency V for the respective metal.

Analysis of Perfume Leakage from Perfume Microcapsules (PMC) in Antiperspirant and Deodorant Products Using Gas Chromatography (GC) and Mass Spectrometry (MS)

All laboratory instruments should be operated according to manufacturers' instructions, as set forth in the instrument operation manuals and instructional materials, unless otherwise indicated.

Sample Preparation and Analysis Principle

For the analysis of perfume that leaked out of the perfume microcapsules in a product, weigh an appropriate amount of the product into the bottom of a 20 mL screw/crimp cap vial. A control is the same product without the microcapsules but with the same amount of free perfume. The same amount of the product is weighed into another 20 ml vial. An appropriate extracted ion is utilized to calculate the respective peak area for each perfume component. A free fragrance control is used to represent 100% leakage. For example, if the area of specific perfume material is 1000 in the control and found to be 500 in a PMC containing sample then that component is calculated to have 50% leakage. Allow sample to equilibrate in vial for a minimum of 8 hours prior to analysis by GC/MS with Solid Phase Microextraction (SPME) sample injection.

Apparatus
1. Laboratory Timer.
2. Gas Chromatograph (GC): Agilent model 6890 or equivalent
3. GC column: Agilent DB-5MS, 30 M×0.250 mm ID, 1.0 μm film thickness obtained from Agilent Technologies, Inc. Wilmington, DE., USA.
4. SPME fiber: Supelco 50/30 mm divinylbenzene/Carboxen on polydimethylsiloxane 2 centimeter.
5. Carrier gas, helium, 1.2 ml/min. flow rate.
6. The Detector is a model Agilent 5975 Mass Selective Detector (or equivalent) obtained from Agilent Technologies, Inc., Wilmington, DE, USA having a source temperature of about 230° C., and a MS Quad temperature of about 150° C.

Analysis Procedure
1. Sample vials place to proper sample tray and proceed with GC-MS analysis.
2. Start sequence of sample loading and analysis. The SPME conditions are: 2 minutes extraction at room temperature and 10 minutes desorption at 270 C. In this step, the GC/MS analysis run is in split/splitless mode with splitless injection. The following temperature program is used:
   i) an initial temperature of about 75° C.
   ii) increase the initial temperature at a rate of about 6° C./min until a temperature of 280° C. is reached, then hold for 3.83 minutes. The total run time is 38 minutes.
3. Perfume compounds are identified using the MS spectral libraries of John Wiley & Sons and the National Institute of Standards and Technology (NIST), purchased and licensed through Agilent Technologies, Inc., Wilmington, DE, USA.
4. Chromatographic peaks for specific ions are integrated using the MassHunter software obtained from Agilent Technologies, Inc., Wilmington, DE, USA.
5. Calculate the leakage of each perfume component by ratio the peak area of the specific ion from the PMC containing product to that of the control. Average of the leakage for all components is reported as the leakage for the perfume.

EXAMPLES

The examples provided below are intended to be illustrative in nature and are not intended to be limiting.

Non-Hydrolytic PEOS Synthesis:

1000 gr of TEOS (available from Sigma Aldrich) was added to a clean dry round bottom flask equipped with a stir bar and distillation apparatus under nitrogen atmosphere. Next, 564 gr of acetic anhydride (available from Sigma Aldrich) and 5.9 gr of Tetrakis(trimethylsiloxide) titanium (available from Gelest, Sigma Aldrich) were added and the contents of the flask and heated to 135 C under stirring. The reaction temperature was maintained at 135 C under vigorous stirring for hours, during which the organic ester generated by reaction of the alkoxy silane groups with acetic anhydride was distilled off along with additional organic esters generated by the condensation of silyl-acetate groups with other alkoxysilane groups which occurred as the polyethoxysilane (PEOS) was generated. The reaction flask was cooled to room temperature and placed on a rotary evaporator (Buchi Rotovapor R110), used in conjunction with a water bath and vacuum pump (Welch 1402 DuoSeal) to remove any remaining solvent. The degree of branching (DB), Molecular weight (Mw) and polydispersity index (PDI) of the PEOS polymer synthetized were respectively 0.42, 2.99 and 2.70.

Example 1. Non-Hydrolytic Precursor Synthesis 1000 g of tetraethoxysilane (TEOS, available from Sigma Aldrich) is added to a clean dry round bottom flask equipped with a stir bar and distillation apparatus under nitrogen atmosphere. 490 ml of acetic anhydride (available from Sigma Aldrich) and 5.8 g of Tetrakis(trimethylsiloxy)titanium (available from Gelest) is added and the contents of the flask are stirred for 28 hours at 135° C. During this time, the ethyl acetate generated by reaction of the ethoxy silane groups with acetic anhydride is distilled off. The reaction flask is cooled to room temperature and is placed on a rotary evaporator (Buchi Rotovapor R110), used in conjunction with a water bath and vacuum pump (Welch 1402 DuoSeal) to remove any remaining solvent and volatile compounds. The polyethoxysilane (PEOS) generated is a yellow viscous liquid with the following specifications found in Table 1. The ratio of TEOS to acetic anhydride can be varied to control the parameters presented in Table 1.

TABLE 1

| Parameters of PEOS | Results |
| --- | --- |
| Degree of branching (DB) | 0.26 |
| Molecular weight (Mw) | 1.2 |
| Polydispersity index (PDI) | 3.9 |

Capsule Synthesis:

Five batches were made following the procedure below, and after the curing step, the 5 batches were combined to yield a combined slurry:

The oil phase was prepared by mixing and homogenizing (or even dissolving if all compounds are miscible) 3 g of the PEOS precursor synthesized above with 2 g of a benefit agent and/or a core modifier, here a fragrance oil. 100 gr of water phase was prepared by mixing 0.5 g of NaCl, 3.5 gr of Aerosil 300 fumed silica from Evonik and 96 gr of DI water. The fumed silica was dispersed in the aqueous phase with an IKA ultra-turrax (S25N) at 20000 RPM for 15 min.

Once each phase was prepared separately, 5 g of the oil phase was dispersed into 16 g of the water phase with an IKA Ultra-Turrax mixer (S25N-10 g) at 25000 RPM for 5 minutes to reach a desired mean oil droplet diameter. Then the pH was brought to 1 using HCl 0.1M added dropwise. Once the emulsification step was complete, the resulting emulsion was left resting without stirring for 4 hours at room temperature, and then 16 hours at 90° C. until enough curing had occurred for the capsules to not collapse. The five batches were combined after the curing step, to obtain a combined capsule slurry.

In order to deposit a second shell component, the combined capsule slurry received a post-treatment with a second shell component solution. 50 g of the combined slurry was diluted with 50 g of 0.1M HCl(aq). The pH was adjusted to 7 using 1M NaOH(aq) added dropwise. Then, the diluted slurry was treated with a controlled addition (40 µl per minute) of the second shell component precursor solution (20 ml of 15 w % of Sodium silicate(aq.)), using a suspended magnetic stirrer reactor at 300 RPM, at room temperature. The pH was kept constant at pH 7 by continuously infusing 1.6M HCl(aq) and 1M NaOH(aq) solutions. Then the capsules were centrifuged per 10 minutes at 2500 RPM. The supernatant was discarded, and the capsules were re-dispersed in de-ionized water.

To test whether capsules collapse, the slurry was diluted 10 times into de-ionized water. Drops of the subsequent dilution were added to a microscopy microslide and left to dry overnight at room temperature. The following day, the dried capsules were observed under an optical microscope by light transmission to assess if the capsules have retained their spherical shape (without the use of a cover slide). The capsules survived drying and didn't collapse. The mean volume weighted diameter of the capsules measured was 5.3 µm with a CoV of 46.2%. The percentage of organic content in the shell was 0%.

Example 2. Synthesis of Capsule Populations

The oil phase is prepared by mixing and homogenizing (or even dissolving if all compounds are miscible) a precursor with a benefit agent and/or a core modifier (percentage of precursor in the total oil core is described in table 2A). The water phase is prepared by adding 1.25 w % Aerosil 300 (available from Evonik) in a 0.1M HCl aqueous solution, dispersed with an ultrasound bath for at least 30 minutes.

Once each phase is prepared separately, they are combined (one part of oil phase to four parts of water), and the oil phase is dispersed into the water phase with IKA ultra-turrax S25N-10G mixing tool at 13400 RPM per 1 minute. Once the emulsification step is complete, the resulting emulsion is cured at different time and temperature combinations (see Table 2A; "RT"=room temperature, approx. 22° C.). In order to deposit a second shell component, the capsules receive a post-treatment with a second shell component solution: the slurry is pre-diluted in 0.1M HCl and treated with a controlled addition of a 10 wt % sodium silicate aqueous solution, using a suspended magnetic stirrer reactor at 350 RPM, at room temperature (details about pre-dilution and infusion rates and quantities of the sodium silicate solution are in table 2A; 25% dilution equals 4 times dilution). The pH is kept constant at pH 7 using 1M HCl(aq) and 1M NaOH(aq) solutions. The capsules are kept under agitation at 300 RPM for 24 hours, then are centrifuged for 10 minutes at 2500 rpm and re-dispersed in de-ionized water.

TABLE 2A

| Capsule Sample ID | Core composition | Precursor percentage in the core | Curing condition | Post-treatment condition |
|---|---|---|---|---|
| Sample A | Perfume 1 | 20% | 21 days at 50° C. | Pre-dilution: 18% Infusion: 40 µl/min. and 0.4 ml/g of slurry |
| Sample B | Perfume 2 | 20% | 4 h at RT, 16 h at 50° C., and 96 h at 70° C. | Pre-dilution: 50% Infusion: 40 µl/min. and 0.16 ml/g of slurry |

TABLE 2A-continued

| Capsule Sample ID | Core composition | Precursor percentage in the core | Curing condition | Post-treatment condition |
|---|---|---|---|---|
| Sample C | Perfume 2 | 33% | 4 h at RT, 16 h at 50° C., and 96 h at 70° C. | Pre-dilution: 50% Infusion: 20 µl/min. and 0.16 ml/g of slurry |

FIG. 1 shows a schematic illustration of the method of making capsules 8 with a first shell component 6, prepared with a hydrophobic core 4. For example, in the first box 100, an oil phase 1 is provided to an aqueous phase 2. The oil phase 2 comprises a hydrophobic benefit agent, such as one or more perfume raw materials, as well as a liquid precursor material. Nanoparticles 3 have surrounded the oil phase 1, for example forming a Pickering emulsion. In the second box 101, a hydrolyzed precursor 5 begins to form at the interface around a core 4, where the core 4 comprises an oil phase that includes the benefit agent. In the third box 102, a first shell component 6 has formed around the core 4, where the first shell component is formed from the nanoparticles 3 and the hydrolyzed precursor 5.

Figure 2:
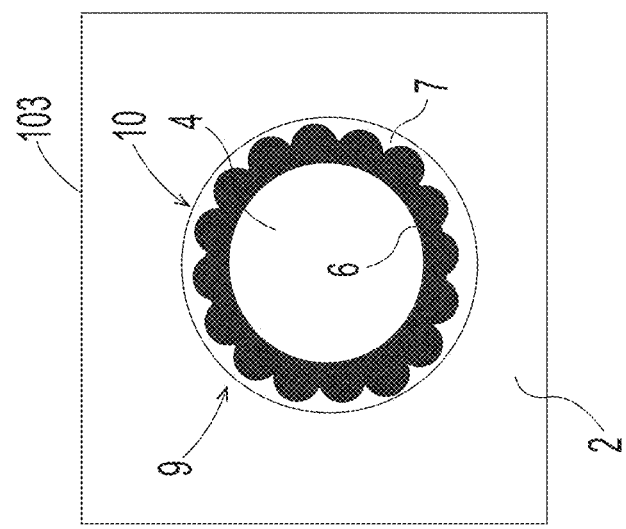
FIG. 2 shows a schematic illustration of a capsule with a first shell component and a second shell component.

FIG. 2 shows a schematic illustration in box 103 of a capsule 9 with a shell 10, the shell 10 having a first shell component 6 and a second shell component 7, around a core 4. The capsule 9 is shown in an aqueous phase 2. The core 4 comprises one or more perfume raw materials. FIG. 3 shows a scanning electron microscopy image of such a capsule 9 in cross-section. A core 4 is surrounded by shell 10, where the shell 10 includes a first shell component 6 surrounded by a second shell component 7.

Table 2B shows some parameters of the capsules of Sample A, Table 2A.

TABLE 2B

| Parameters | Sample A results |
|---|---|
| Mean Diameter (um) | 27.8 |
| CoV PSD (%) | 26.7 |
| Shell % organic | 0% |

Example 3. Comparison of Leakage of Different Types of Capsules

Figure 4:
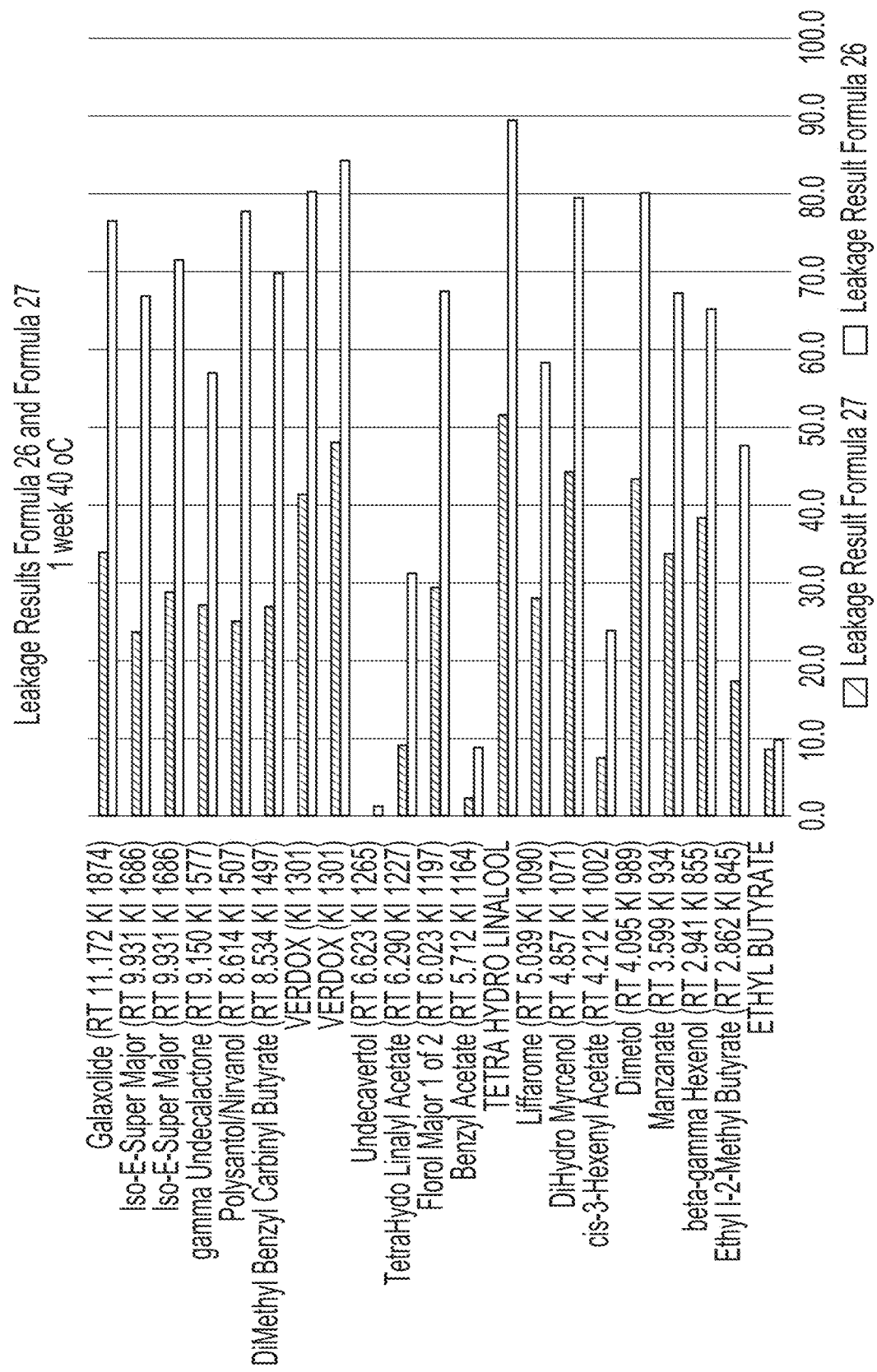
FIG. 4 shows the leakage results of PRMs from inventive microcapsules.

Clear Gel antiperspirants described in Formula 26 and Formula 27 from example 12 were prepared and placed in 5° C. and 40° C. to age for 1 week prior to analysis on the leakage method for deodorant compositions. After 1 week, the Formula 25 and Formula 26 samples containing the inventive microcapsules were analyzed using the test method Analysis of Perfume Leakage from Perfume Microcapsules (PMC) in Antiperspirant and Deodorant Products Using Gas Chromatography (GC) and Mass Spectrometry (MS), as described herein. The inventive microcapsules were inorganic fragrance capsules with two different levels of polyoxysiloxane which comprised various perfume raw materials. In FIG. 4, the left axis shows the perfume raw materials that were analyzed, along with their respective retention time (RT) and kovats index (KI) shown in parentheses. The bottom axis shows the % leakage. The results showed that the product containing the inventive microcapsules comprising 20% polyoxysiloxane in the oil phase had greater degree of leakage vs. the product containing the inventive microcapsules comprising 33% polyoxysiloxane in the oil phase.

The aged samples were also evaluated by two expert graders according to the following method:

0.25 g Formula 26, Formula 27, and Formula 28 from Example 12 were applied to a perfume blotter card and evaluated by an expert grader using the following intensity scale:

Intensity Scale: 100—Very Strong, 75—Strong, 50—Moderate, 25—Slight, 0—No Odor

At 8 hours, a separate blotter is folded, and the ends then rubbed together. The rubbed blotter is compared to the original dry blotter to judge intensity difference. The results show that the inorganic fragrance capsule of the claimed invention displays significant intensity increase compared to the unrubbed blotter card.

The sample with 33% polyethoxysiloxane in the oil phase has more release of perfume with friction and less leakage compared to the sample containing 20% polyethoxysiloxane in the oil phase.

| Reference | Conditions | % Leakage | 8-hour Pre/Post-rub Grader 1 | 8-hour Pre/Post-rub Grader 2 |
|---|---|---|---|---|
| Formula 28 | 5° C. | n/a | 45+/+0/5 | 45+/+0/5 |
| Formula 26 containing inorganic fragrance capsulese in water comprising 20% polyethoxysiloxane | 5° C. | 58 | 45 +0/5 | 40/ +0/5 |
| | 40° C. (1 Week) | 58 | 40 +0/5 | 40/ +0 |
| Formula 27 containing inorganic fragrance capsules in water 33% polyethoxysiloxane | 5° C. | 32 | 40+ +10 green fruity | 35+/ +5/10 Green |
| | 40° C. (1 Week) | 27 | 40+/ +5/10 green fruity | 35+/ +5 |

Example 4: Capsule Leakage and Performance in Glycol Deodorant

Glycol deodorants described in Formula 8 and Formula 9 from example 7 were prepared aged at 25° C. for 1 month prior to analysis on the leakage method for deodorant compositions. After 1 month, Formula 9 containing the inventive microcapsules were analyzed using the test method Analysis of Perfume Leakage from Perfume Microcapsules (PMC) in Antiperspirant and Deodorant Products Using Gas Chromatography (GC) and Mass Spectrometry (MS), as described herein. The inventive microcapsules were inorganic fragrance capsules made with 33% polyoxysiloxane which comprised various perfume raw materials. The results showed that the product containing the inventive microcapsules had an average leakage of 50.1%

The aged samples were also evaluated by two expert graders according to the following method:

0.25 g Formula 8, and Formula 9 from Example 7 were applied to a perfume blotter card and evaluated by an expert grader using the following intensity scale:

Intensity Scale: 100—Very Strong, 75—Strong, 50—Moderate, 25—Slight, 0—No Odor

At 8 and 24 hours, a separate blotter is folded, and the ends then rubbed together. The rubbed blotter is compared to the original unrubbed blotter to judge intensity difference. The results show that the inorganic fragrance capsule of the claimed invention displays significant intensity increase compared to the unrubbed blotter card.

At 8 and 24 hours, a separate blotter is wetted with water. The wetted blotter is compared to the original dry blotter. The results show that the inorganic capsule of the claimed invention displays significant increase compared to the unwetted blotter card.

The sample with the inventive capsules has more release of perfume with friction compared to the comparative sample from formula 8

| Reference | Conditions | Initial Grade Dry Within 10 Min after applying | 8 Hr Grade Dry | 8 Hr Grade | 8 Hr Rubbed | 8 Hr Wetted | 24 hr | 24 Hr Rubbed | 24 Hr Wetted |
|---|---|---|---|---|---|---|---|---|---|
| Formula 8 reference not comprising inventive capsule | 25° C. (1 month) | 75 | 55 | 75 | +0 | +0 | 40 | +0 | +0 |
| Formula 9 comprising inventive capsules | 25° C. (1 month) | 75 | 55 | 75 | +5-10 | +0-5 | 55 | +10 | +5 |

EXAMPLES

Example 5: Clear Gel Antiperspirant and Deodorant Compositions

|  | Formula 1 Clear Gel | Formula 2 Clear Gel | Formula 3 Clear Gel | Formula 4 Clear Gel |
|---|---|---|---|---|
| Water | Q.S. | Q.S. | Q.S. | Q.S. |
| Aluminum Zirconium Octachlorohydrex Gly, (16% in water) | 55.2 | 55.2 | 55.2 | 24.2 |
| Alcohol Denat. | 11.9 | 11.86 | — | 11.9 |
| Propylene Glycol | 7.7 | 7.7 | — | 28.2 |
| Dipropylene Glycol | — | — | 12 | — |
| PEG/PPG-18/18 Dimethicone | 7.8 | 7.8 | 3.8 | 7.8 |
| Dimethicone | 5.6 | 5.6 | 12.2 | 3.6 |
| Cyclopentasiloxane | 2.8 | 2.8 | — | 5.1 |
| Fragrance | — | — | 0.5 | 0.4 |
| Inorganic Fragrance Capsule in water | 2.0 | — | 1.0 | 0.75 |
| Comparative Fragrance Capsule in water | — | 2.0 | — | — |

Q.S.—indicates that this material is used to bring the total to 100%.

Samples of Formula 1 from Example 5 comprising the inorganic capsule of the claimed invention was stored at 5° C. and also at 40° C. for 1 month. Formula 2 from Example 4 comprising a comparative capsule was made fresh for the following experiment:

0.25 g Formula 1 and Formula 2 from Example 5 were applied to a perfume blotter card and evaluated by an expert grader using the following intensity scale:

Intensity Scale: 100—Very Strong, 75—Strong, 50—Moderate, 25—Slight, 0—No Odor

At 8 hours and 24 hours, a separate blotter is folded, and the ends then rubbed together. The rubbed blotter is compared to the original dry blotter to judge intensity difference. The results show that the inorganic fragrance capsule of the claimed invention displays significant intensity increase compared to the unrubbed blotter card. Furthermore, the comparative capsule showed very little intensity increase compared to the unrubbed blotter card.

| Product Matrix | Initial Grade Dry Within 10 Min after applying | 8 Hr Grade Dry | 8 Hr Grade Rubbed (intensity increase) | 24 Hr Dry | 24 Hr Grade Rubbed (intensity increase) |
|---|---|---|---|---|---|
| Formula 1 from Example 1 comprising the claimed invention (Storage 1 Month at 5° C.) | 65+ Orange flower | 50 | +10 Orange flower, fruity | 25 | +15 Orange flower |
| Formula 1 from Example 1 comprising the claimed invention (Storage 1 Month at 40° C.) | 60+ Orange flower, sl. more wintergreen | 45+ | +10 Orange flower, fruity | 20 | +15 Orange flower |
| Formula 2 from Example 1 containing comparative capsule (Product tested as freshly made) | 65 Floral green powdery | 40+ | +0/5 Sl. greener? | 20/25 | +0 |

Example 6: Soft Solid Antiperspirant Compositions

|  | Formula 5 Soft Solid | Formula 6 Soft Solid | Formula 7 Soft Solid |
|---|---|---|---|
| Cyclopentasiloxane | Q.S. | Q.S. | Q.S. |
| Aluminum Zirconium Trichlorohydrex Glycine Powder | 26.5 | 26.5 | 26.5 |
| Dimethicone | 5 | 7.5 | 6 |
| Tribehenin | 4.5 | 4 | 4 |
| C 18-36 acid triglyceride | 1.1 | 1.4 | 1 |
| PPG-14 Butyl Ether | 0.5 | 0.5 | 0.5 |
| White Petrolatum | 3 | 2.5 | 3.5 |
| Perfume | 1 | 1.25 | 0.75 |
| Inorganic Fragrance Capsule | 0.6 | 0.5 | 0.75 |

Q.S.—indicates that this material is used to bring the total to 100%.

Example 7: Glycol Deodorant Compositions

| Ingredient | Formula 8 Solid Deodorant | Formula 9 Solid Deodorant | Formula 10 Solid Deodorant | Formula 11 Solid Deodorant |
|---|---|---|---|---|
| Water | Q.S. | Q.S. | Q.S. | Q.S. |
| dipropylene glycol | 45.5 | 45.5 | 20.0 | 30.0 |
| propylene glycol | 19.0 | 19.0 | 22.0 | — |
| tripopylene glycol | — | — | 25.0 | — |
| Glycerine | — | — | — | 10.0 |
| PEG-8 | — | — | — | 20.0 |
| sodium stearate | 5.0 | 5.0 | 5.5 | 5.5 |
| Partially Carbonated Magnesium Hydroxide | — | 8.0 | 8.0 | — |
| tetra sodium EDTA | 0.41 | 0.41 | 0.5 | 0.05 |
| Poloxamine 1307 | 3.0 | 3.0 | — | — |
| PPG-3 Myristyl Ether | 1.39 | 1.39 | — | — |
| Aminomethyl Propanol | — | — | — | — |
| Fragrance | 3.1 | 3.1 | 1.0 | 0.5 |
| Inorganic Fragrance Capsule | — | 0.75 | 0.6 | 0.8 |
| Blue 1 | 0.0009 | 0.0009 | — | — |

Q.S.—indicates that this material is used to bring the total to 100%.

Example 8: Body Spray Compositions

| Ingredient | Formula 12 Body Spray | Formula 13 Body Spray | Formula 14 Body Spray | Formula 15 Body Spray |
|---|---|---|---|---|
| Water | Q.S. | Q.S. | Q.S | Q.S. |
| Denatured Alcohol | 35.5 | 60.0 | 60.0 | 70.0 |
| Dipropylene Glycol | 15.0 | — | — | 15.0 |
| Cavasol W7 methylated Beta-cyclodextrin | — | 1.0 | 1.0 | — |

-continued

| Ingredient | Formula 12 Body Spray | Formula 13 Body Spray | Formula 14 Body Spray | Formula 15 Body Spray |
|---|---|---|---|---|
| Fragrance | 2.0 | 1.75 | 2.5 | 3.5 |
| Inorganic Fragrance Capsule | 1.00 | 0.75 | 1.5 | 1.0 |
| Propane | 4.9 | — | — | — |
| Isobutane | 27.1 | — | — | — |
| 1,1-Difluoroethane (HFC-152a) | 8.0 | 35.0 | 35.0 | — |

Q.S.—indicates that this material is used to bring the total to 100%.

Example 9: Solid Stick Emulsified Antiperspirant Compositions

| Ingredient | Formula 16 Emulsified Stick | Formula 17 Emulsified Stick | Formula 18 Emulsified Stick |
|---|---|---|---|
| Hexamethyldilsiloxane | 21.25 | 21.25 | 21.25 |
| Lauryl PEG/PPG-18/18 Methicone | 1.2 | 1.2 | — |
| Fragrance | 2.25 | 1.5 | 2.0 |
| Lauryl PEG/PPG-18/18 Methicone | — | — | 1.2 |
| ACH (40% Solution) | 55.0 | — | — |
| IACH (34% Solution) | — | 49.0 | — |
| ZAG (30% Solution) | — | — | 52.3 |
| Propylene Glycol | 5.0 | 5.0 | 5.0 |
| Water | Q.S. | Q.S. | Q.S. |
| Inorganic Fragrance Capsule | 1.0 | 0.75 | 1.25 |
| Finsolv TN | 6.5 | 6.0 | 6.5 |
| Ozokerite Wax | — | — | 12.0 |
| Performalene PL | 12.0 | 12.0 | — |

Example 10: Invisible Solid Compositions

| Ingredient | Formula 19 Invisible Solid | Formula 20 Invisible Solid | Formula 21 Invisible Solid | Formula 22 Invisible Solid |
|---|---|---|---|---|
| Aluminum Zirconium Trichlorohydrex Glycine Powder | 25.6 | 25.6 | 25.6 | 24.0 |
| Cyclopentasiloxane | Q.S | Q.S. | Q.S. | — |
| Dimethicone | — | — | 5 | Q.S. |
| CO-1897 Stearyl Alcohol NF | 13 | 14 | 13 | 13.5 |
| Hydrogenated Castor Oil MP80 Deodorized | 2.9 | 3.5 | 2.9 | 2.75 |
| Behenyl Alcohol | 0.2 | 0.25 | 0.2 | 0.2 |
| Ozokerite Wax SP-1026 | — | 1.0 | — | — |
| PEG-8 Distearate | — | — | — | 2.0 |
| C12-15 Alkyl Benzoate | 8.5 | 8.5 | — | 10.0 |
| PPG-14 Butyl Ether | 6.5 | 6.5 | 3 | 3 |
| Phenyl Trimethicone | — | — | — | 5.0 |
| Mineral Oil | 1.0 | 1.0 | 8.0 | 10.0 |
| Talc Imperial 250 USP | 2.5 | — | 3 | 7 |
| Fragrance | 1.5 | 2.0 | 0.75 | 1.25 |
| Inorganic Fragrance Capsule | 1.5 | 1.0 | 1.25 | 1.25 |
| Fragrance Complexed Beta-cyclodextrin | — | 2 | — | — |

Example 11: Aerosol AP Compositions

| Ingredient | Formula 23 Aerosol Antiperspirant | Formula 24 Aerosol Antiperspirant | Formula 25 Aerosol Antiperspirant |
|---|---|---|---|
| Cyclopentasiloxane | Q.S. | — | — |
| Dimethicone | — | Q.S. | Q.S. |
| Isopropyl Myristate | — | — | 1.8 |
| Disteardimonium Hectorite | 0.85 | 0.85 | 0.85 |
| Triethyl Citrate | 0.28 | 0.28 | 0.28 |
| Aluminum Chlorohydrate Powder | 5.27 | 5.27 | 5.27 |
| BCD Fragrance Complex | 0.6 | 0.6 | 0.6 |
| Tapioca Starch | 2.4 | 2.4 | 2.4 |
| Dimethicone (and) Dimethiconol | 0.1 | 0.1 | 0.1 |
| Fragrance | 1.1 | 1.3 | 1.1 |
| Inorganic Fragrance Capsule | 1.0 | 1.5 | 0.75 |
| aeropress A46 Propellant | 80.0 | 80.0 | 80.0 |

Example 12: Clear Gel Antiperspirant Compositions Containing Ethanol

| Ingredient | Formula 26 Clear Gel | Formula 27 Clear Gel | Formula 28 Clear Gel |
|---|---|---|---|
| Water | Q.S. | Q.S. | Q.S. |
| Aluminum Zirconium Octachlorohydrex Gly, (16% in water) | 55.2 | 55.2 | 55.2 |
| Alcohol Denat. | 11.9 | 11.9 | 11.86 |
| Propylene Glycol | 7.7 | 7.7 | 7.7 |
| PEG/PPG-18/18 Dimethicone | 7.8 | 7.8 | 7.8 |
| Dimethicone | 5.6 | 5.6 | 5.6 |
| Cyclopentasiloxane | 2.8 | 2.8 | 2.8 |
| Fragrance | — | — | 0.13 |
| Inorganic Fragrance Capsule in water comprising 20% poly-ethoxy siloxane | 1.00 | — | — |
| Inorganic Fragrance Capsule in water comprising 33% poly-ethoxy siloxane | — | 1.22 | — |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An antiperspirant or deodorant composition comprising a population of capsules,
    the capsules comprising a core and a shell surrounding the core,
    wherein the core comprises perfume raw materials,
    wherein the shell comprises:
        a substantially inorganic first shell component comprising
            a condensed layer and a nanoparticle layer,
                wherein the condensed layer comprises a condensation product of a precursor,
            wherein the nanoparticle layer comprises inorganic nanoparticles, and
            wherein the condensed layer is disposed between the core and the nanoparticle layer;
        an inorganic second shell component surrounding the first shell component, wherein the second shell component surrounds the nanoparticle layer;
    wherein the precursor comprises at least one compound from the group consisting of Formula (I), Formula (II), and a mixture thereof,
    wherein Formula (I) is $(M'O_zY_n)_w$,
    wherein Formula (II) is $(M'O_zY_nR^1_p)_w$,
    wherein for Formula (I), Formula (II), or the mixture thereof:
        each M is independently selected from the group consisting of silicon, titanium, and aluminum,
        v is the valence number of M and is 3 or 4,
        z is from 0.5 to 1.6,
        each Y is independently selected from —OH, —OR², halogen,

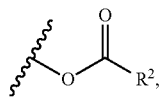

—NH₂, —NHR², —N(R²)₂, and

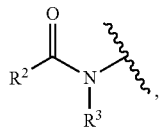

wherein R² is a $C_1$ to $C_{20}$ alkyl, $C_1$ to $C_{20}$ alkylene, $C_6$ to $C_{22}$ aryl, or a 5-12 membered heteroaryl, wherein the heteroaryl comprises from 1 to 3 ring heteroatoms selected from O, N, and S, wherein R³ is a H, $C_1$ to $C_{20}$ alkyl, $C_1$ to $C_{20}$ alkylene, $C_6$ to $C_{22}$ aryl, or a 5-12 membered heteroaryl, wherein the heteroaryl comprises from 1 to 3 ring heteroatoms selected from O, N, and S, w is from 2 to 2000;
wherein for Formula (I),
    n is from 0.7 to (v−1); and
wherein for Formula (II),
    n is from 0 to (v−1),
    each R¹ is independently selected from the group consisting of: a $C_1$ to $C_{30}$ alkyl; a $C_1$ to $C_{30}$ alkylene; a $C_1$ to $C_{30}$ alkyl substituted with a member selected from the group consisting of a halogen, —OCF₃, —NO₂, —CN, —NC, —OH, —OCN, —NCO, alkoxy, epoxy, amino, mercapto, acryloyl, —CO₂H, —C(O)-alkyl, —C(O)O-aryl, and —C(O)O-heteroaryl; and a $C_1$ to $C_{30}$ alkylene substituted with a member selected from the group consisting of a halogen, —OCF₃, —NO₂, —CN, —NC, —OH, —OCN, —NCO, alkoxy, epoxy, amino, mercapto, acryloyl, —C(O)OH, —C(O)O-alkyl, —C(O)O-aryl, and —C(O)O-heteroaryl; and
    p is a number that is greater than zero and is up to pmax, wherein $p\,\text{max}=60/[9*Mw(R^1)+8]$, wherein Mw(R¹) is the molecular weight of the R¹ group.

2. The composition of claim 1, wherein the precursor comprises at least one compound according to Formula (I).

3. The composition claim 1, wherein the precursor comprises at least one compound according to Formula (II).

4. The composition of claim 1, wherein the population of capsules is characterized by one or more of the following:
    (a) a mean volume weighted capsule diameter of about 10 μm to about 200 μm;
    (b) an average shell thickness of about 170 nm to about 1000 nm;
    (c) a volumetric core/shell ratio of from about 50:50 to 99:1;
    (d) the first shell component comprises no more than about 5% of organic content, by weight of the first shell component; or
    (e) a mixture thereof.

5. The composition of claim 1, wherein the compounds of Formula (I), Formula (II), or both are characterized by one or more of the following:
    (a) a Polystyrene equivalent Weight Average Molecular Weight (Mw) of from about 700 Da to about 30,000 Da;

(b) a degree of branching of 0.2 to about 0.6;
(c) a molecular weight polydispersity index of about 1 to about 20; or
(d) a mixture thereof.

6. The composition of claim 1, wherein for Formula (I), Formula (II), or both, M is silicon.

7. The composition of claim 1, wherein for Formula (I), Formula (II), or both, Y is OR, wherein R is selected from a methyl group, an ethyl group, a propyl group, or a butyl group.

8. The composition of claim 1, wherein the second shell component comprises a material selected from the group consisting of calcium carbonate, silica, and a combination thereof.

9. The composition of claim 1, wherein the inorganic nanoparticles of the first shell component comprise at least one of metal nanoparticles, mineral nanoparticles, metal-oxide nanoparticles and/or semi-metal oxide nanoparticles.

10. The composition of claim 1, wherein the inorganic second shell component comprises at least one of $SiO_2$, $TiO_2$, $Al_2O_3$, $CaCO_3$, $Ca_2SiO_4$, $Fe_2O_3$, $Fe_3O_4$, iron, silver, nickel, gold, copper, and/or clay.

11. The composition of claim 1, further comprising ethanol.

12. The composition of claim 1, further comprising from about 5% to about 10%, by weight of the composition, ethanol.

13. The composition of claim 1, further comprising at least about 5%, by weight of the composition, water.

14. The composition of claim 1, further comprising at least about 70%, by weight of the composition, water.

15. The composition of claim 1, wherein the composition comprises an emulsion.

16. The composition of claim 1, wherein the composition is substantially without water.

17. The composition of claim 1, further comprising at least about 25%, by weight of the composition, of a glycol.

18. The composition of claim 1, further comprising a short-chain alcohol.

19. The composition of claim 1, wherein the composition is substantially free of an antiperspirant active.

20. The composition of claim 1, wherein the composition is substantially free of cyclopentasiloxane.

* * * * *